US010124173B2

(12) United States Patent
Bonnet et al.

(10) Patent No.: US 10,124,173 B2
(45) Date of Patent: Nov. 13, 2018

(54) SYSTEM FOR STIMULATION THERAPY OF THE VAGUS NERVE BY IMPLEMENTATION OF A SELF-ADAPTIVE STATE TRANSITION MODEL BASED ON PHYSICAL OR PHYSIOLOGICAL LEVELS

(71) Applicants: SORIN CRM SAS, Clamart (FR); UNIVERSITE DE RENNES 1, Rennes (FR); INSERM-INSTITUT DE LA RECHERCHE MEDICALE, Paris (FR)

(72) Inventors: Jean-Luc Bonnet, Massy (FR); Alfredo Hernandez, Cesson Sévigné (FR); Guy Carrault, Cesson-Sévigné (FR); Hector Romero, Rennes (FR); Virginie Le Rolle, Cesson-Sévigné (FR)

(73) Assignees: SORIN CRM SAS, Clamart (FR); UNIVERSITE DE RENNES 1, Rennes (FR); INSERM- INSTITUT DE LA RECHERCHE MEDICALE, Paris (FR)

( * ) Notice: Subject to any disclaimer, the term of this patent is extended or adjusted under 35 U.S.C. 154(b) by 37 days.

(21) Appl. No.: 15/195,753

(22) Filed: Jun. 28, 2016

(65) Prior Publication Data
US 2016/0375250 A1    Dec. 29, 2016

(30) Foreign Application Priority Data
Jun. 29, 2015   (FR) ...................................... 15 56049

(51) Int. Cl.
*A61N 1/36*   (2006.01)
*G16H 50/20*   (2018.01)
(Continued)

(52) U.S. Cl.
CPC ....... *A61N 1/36139* (2013.01); *A61N 1/0551* (2013.01); *A61N 1/365* (2013.01);
(Continued)

(58) Field of Classification Search
None
See application file for complete search history.

(56) References Cited

U.S. PATENT DOCUMENTS 7,463,927 B1  12/2008  Chaouat
7,509,166 B2   3/2009  Libbus
(Continued)

FOREIGN PATENT DOCUMENTS

EP      1 102 607       5/2001
WO    WO-86/05698     10/1986
(Continued)

OTHER PUBLICATIONS

Arabi, et al., Seizure prediction in intracranial EEG: A patient-specific rule-based approach, Engineering in Medicine and Biology Society, EMBC, 2011 Annual International Conference of the IEEE, Aug. 30, 2011, 4 pages.
(Continued)

*Primary Examiner* — Ankit D Tejani
(74) *Attorney, Agent, or Firm* — Foley & Lardner LLP

(57) ABSTRACT

One system includes a stimulation device such as a vagus nerve stimulation lead, and a controller for controlling the stimulation device according to a set of stimulation parameters. A memory of the stimulation device contains a state transition model, and for each state defines a set of stimulation parameters and at least one expected response during the application of stimulation with the parameters. A matrix determines the transition rules between states based on physiological levels measured versus target levels. A state transition control unit determines, in an organized timely
(Continued)

method, possible transitions between states according to the rules on physiological levels obtained in response to the implementation of the stimulation parameters of the current state, and a transition from a current state to a new state causes a corresponding change in the parameter set used for stimulation.

21 Claims, 14 Drawing Sheets

(51) Int. Cl.
*A61N 1/365* (2006.01)
*A61N 1/05* (2006.01)
G16H 50/50 (2018.01)
A61B 5/00 (2006.01)
A61N 1/372 (2006.01)
G06F 19/00 (2018.01)
A61B 5/0205 (2006.01)

(52) U.S. Cl.
CPC ..... *A61N 1/36053* (2013.01); *A61N 1/36125* (2013.01); *A61N 1/36146* (2013.01); *A61N 1/37235* (2013.01); *G06F 19/345* (2013.01); *G16H 50/20* (2018.01); *A61B 5/0205* (2013.01); *A61B 5/4836* (2013.01); *A61B 5/686* (2013.01); *A61N 1/36114* (2013.01); *A61N 1/36157* (2013.01); *A61N 1/36175* (2013.01); *A61N 1/36178* (2013.01); *A61N 1/36521* (2013.01); *A61N 1/36535* (2013.01); *A61N 1/36542* (2013.01); *A61N 1/36564* (2013.01); *A61N 1/36571* (2013.01); *A61N 1/36578* (2013.01); *A61N 1/36585* (2013.01); *A61N 1/36592* (2013.01); *A61N 1/37247* (2013.01); *G06F 19/3437* (2013.01); *G16H 50/50* (2018.01)

(56) References Cited

U.S. PATENT DOCUMENTS

| 7,783,349 | B2 | 8/2010 | Libbus et al. |
|---|---|---|---|
| 2004/0230105 | A1 | 11/2004 | Geva et al. |
| 2005/0119703 | A1 | 6/2005 | DiLorenzo |
| 2005/0216071 | A1 | 9/2005 | Devlin et al. |
| 2005/0240242 | A1 | 10/2005 | DiLorenzo |
| 2006/0293720 | A1 | 12/2006 | DiLorenzo |
| 2007/0067003 | A1 | 3/2007 | Sanchez et al. |
| 2008/0051839 | A1 | 2/2008 | Libbus et al. |
| 2009/0326624 | A1 | 12/2009 | Melse |
| 2010/0211135 | A1 | 8/2010 | Caparso et al. |
| 2010/0241020 | A1 | 9/2010 | Zaidel et al. |
| 2012/0016435 | A1 | 1/2012 | Rom |
| 2012/0245656 | A1 | 9/2012 | Brockway et al. |
| 2013/0274625 | A1 | 10/2013 | Sarma et al. |
| 2013/0317580 | A1 | 11/2013 | Simon et al. |
| 2014/0057232 | A1 | 2/2014 | Wetmore et al. |
| 2014/0074180 | A1 | 3/2014 | Heldman et al. |
| 2014/0288620 | A1 | 9/2014 | DiLorenzo |
| 2014/0358024 | A1 | 12/2014 | Nelson et al. |
| 2015/0005680 | A1 | 1/2015 | Lipani |
| 2015/0012057 | A1 | 1/2015 | Carlson et al. |

FOREIGN PATENT DOCUMENTS

| WO | WO-2007/141345 | 12/2007 |
|---|---|---|
| WO | WO-2011/137029 | 11/2011 |

OTHER PUBLICATIONS

Capel et al., Artificial Pancreas Using a Personalized Rule-Based Controller Achieves Overnight Normoglycemia in Patients with Type 1 Diabetes, Diabetes Technology & Therapeutics, vol. 16, No. 3, Mar. 2014, 8 Pages.

Poree, et al., Surface Electrocardiogram Reconstruction From Intracardiac Electrograms Using a Dynamic Time Delay Artificial Neural Network, Biomedical Engineering, IEEE Transactions, vol. 60, No. 1, Jan. 2013, 9 pages.

Preliminary Search Report for French Patent Application No. 1556045, dated Feb. 2, 2016, 2 pages.

Preliminary Search Report for French Patent Application No. 1556049, dated May 13, 2016, 2 pages.

Preliminary Search Report for French Patent Application No. 1556057, dated Feb. 3, 2016, 2 pages.

Preliminary Search Report for French Patent Application No. 1556061, dated May 2, 2016, 2 pages.

Löhning, et al., Model predictive control using reduced order models: Guaranteed stability for constrained linear systems, Journal of Process Control, vol. 24, No. 11, Nov. 2014, 13 pages.

Romero Ugalde, et al., Neural network design and model reduction approach for black box nonlinear system identification with reduced number of parameters, Neurocomputing, vol. 101, Feb. 4, 2013, 11 pages.

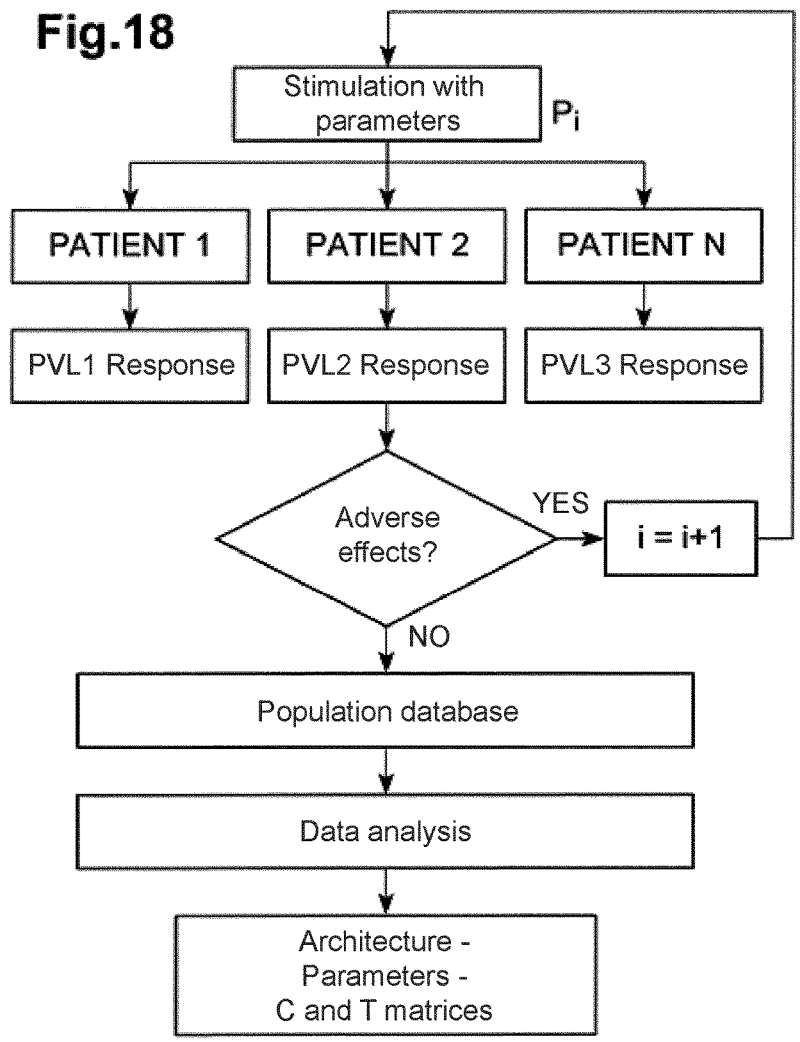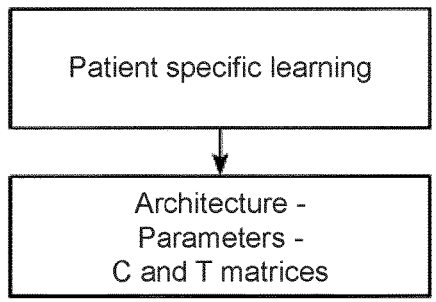

Fig.22

| N | Period | Amplitude |
|---|---|---|
| P0,0 = 0 | P0,1 = 0 | P0,2 = 0 |
| P1,0 = 1 | P1,1 = 22 | P1,2 = 1 |
| P2,0 = 2 | P2,1 = 12 | P2,2 = 1 |
| P3,0 = 2 | P3,1 = 34 | P3,2 = 1 |
| P4,0 = 2 | P4,1 = 21 | P4,2 = 1 |
| P5,0 = 3 | P5,1 = 22 | P5,2 = 1 |
| P6,0 = 3 | P6,1 = 23 | P6,2 = 1 |
| P7,0 = 3 | P7,1 = 38 | P7,2 = 1 |
| P8,0 = 4 | P8,1 = 22 | P8,2 = 1 |
| P9,0 = 4 | P9,1 = 30 | P9,2 = 1 |
| P10,0 = 4 | P10,1 = 38 | P10,2 = 1 |
| P11,0 = 1 | P11,1 = 22 | P11,2 = 2 |
| P12,0 = 2 | P12,1 = 22 | P12,2 = 2 |
| P13,0 = 2 | P13,1 = 30 | P13,2 = 2 |
| P14,0 = 2 | P14,1 = 38 | P14,2 = 2 |
| P15,0 = 3 | P15,1 = 22 | P15,2 = 2 |
| P16,0 = 3 | P16,1 = 30 | P16,2 = 2 |
| P17,0 = 3 | P17,1 = 30 | P17,2 = 2 |
| P18,0 = 4 | P18,1 = 22 | P18,2 = 2 |
| P19,0 = 4 | P19,1 = 30 | P19,2 = 2 |
| P20,0 = 4 | P20,1 = 30 | P20,2 = 2 |
| P21,0 = 1 | P21,1 = 22 | P21,2 = 3 |
| P22,0 = 2 | P22,1 = 22 | P22,2 = 3 |
| P23,0 = 2 | P23,1 = 30 | P23,2 = 3 |
| P24,0 = 2 | P24,1 = 38 | P24,2 = 3 |
| P25,0 = 3 | P25,1 = 22 | P25,2 = 3 |
| P26,0 = 3 | P26,1 = 30 | P26,2 = 3 |
| P27,0 = 3 | P27,1 = 38 | P27,2 = 3 |
| P28,0 = 4 | P28,1 = 22 | P28,2 = 3 |
| P29,0 = 4 | P29,1 = 30 | P29,2 = 3 |
| P30,0 = 4 | P30,1 = 38 | P30,2 = 3 |

SYSTEM FOR STIMULATION THERAPY OF THE VAGUS NERVE BY IMPLEMENTATION OF A SELF-ADAPTIVE STATE TRANSITION MODEL BASED ON PHYSICAL OR PHYSIOLOGICAL LEVELS

CROSS-REFERENCE TO RELATED PATENT APPLICATIONS

This application claims the benefit of and priority to French Patent Application No. 1556049, filed Jun. 29, 2015, which is incorporated herein by reference in its entirety.

BACKGROUND

The disclosure relates generally to devices for applying stimulation of organs for therapeutic purposes.

It is applicable to "active implantable medical devices" as defined by the Directive 90/385/EEC of 20 Jun. 1990 of the Council of the European Communities. This includes devices for continuously monitoring heart activity and for delivering, electrical stimulation, resynchronization and/or defibrillation pulses to the heart, in the event of a rhythm disorder detected by the device. It also includes neurological devices, cochlear implants, etc., as well as devices for pH or other intracorporeal parameter measurements.

Regardless of the pathology to be treated, pacing therapy is usually done to maximize therapeutic effects, while minimizing side effects and the energy consumption in the case where the stimulation is implemented in an autonomous implantable device.

This stimulation may take into account the dynamics of the pathology resulting for example from such an alteration of the autonomic nervous system (ANS), from cardiac or ANS remodeling, as well as from the therapy response (habituation, changes in the electrode-vagus nerve coupling in the case of vagus nerve stimulation (VNS)).

Thus, the application of optimal stimulation is complex, currently addressed imperfectly, although the application of optimal stimulation represents one of the highest priorities in the progress of neurostimulation.

At present, approaches to control of the stimulation in a closed loop can be classified into two families:
1) rules-based approaches, such as those described in U.S. Pat. No. 7,783,349 B2, U.S. Pat. No. 7,509,166 B2, US 2012/245656 A1 or WO 2011/137029 A; or
2) approaches based on a linear or non-linear transfer function of control variables, such as those described for example in EP 1102607 A1.

The first approach has two major limitations: i) it is difficult to define optimal rules for a given patient and ii) these rules are based on the definition of thresholds, which vary depending on the inter-patient and intra-patient variability.

The main limitations of the second approach are i) the computational complexity required to implement the controller, and ii) the amount of data required to adjust the parameters of the controller.

There are also other methods to estimate a set of rules specific to patients [1,2], to infer inter-patient or intra-patient adjustments [3], and to reduce the complexity of the calculations to be performed in the controller [4, 5]. However, these approaches remain theoretical and difficult to implement and integrate into active implantable devices with limited digital processing power. Relevant references are:

[1] A. Aarabi, and H. Bin, "Seizure prediction in intracranial EEG: A patient-specific rule-based approach", *Engineering in Medicine and Biology Society, EMBC,* 2011 *Annual International Conference of the IEEE,* 2566-2569, Boston, Mass.;

[2] I. Capel, M. Rigla, G. García-Sáez, A. Rodríguez-Herrero, B. Pons, D. Subías, F. García-García, M. Gallach, M. Aguilar, C. Pérez-Gandia, E. J. Gómez, A. Caixás, and M. E. Hernando, "Artificial Pancreas Using a Personalized Rule-Based Controller Achieves Overnight Normoglycemia in Patients with Type 1 Diabetes", *Diabetes Technol Ther.,* Vol. 16(3): 172-179 (2014);

[3] F. Porée, A. Kachenoura, G. Carrault, R. D. Molin, P. Mabo, and A. I. Hernández, "Surface Electrocardiogram Reconstruction From Intracardiac Electrograms Using a Dynamic Time Delay Artificial Neural Network", *Biomedical Engineering, IEEE Transactions on,* Vol. 60, 106-114, (2013).

[4] H. M. Romero Ugalde, J.-C. Carmona, V. M. Alvarado and J. Reyes-Reyes, "Neural Network Design and Model Reduction Approach for Black Box Non Linear System Identification with Reduced Number of Parameters", *Neurocomputing,* Vol. 101, 170-180 (2013).

[5] M. Löhning, M. Reble, J. Hasenauer, S. Yu, F. Allgöwer, "Model predictive control using reduced order models: Guaranteed stability for constrained linear systems", *Journal of Process Control,* Vol. 24 (11), 1647-1659, (2014).

Finally, another major limitation of the existing approaches is related to the time constant of the closed loop control. It is usually fixed to a single predefined time scale (e.g. every heartbeat, every minute, every day, etc.), particularly in the case where the controlled variables are the results of the processes that are intermingled on different time scales, as in physiology.

The present disclosure aims to overcome these limitations of the prior art and to provide a stimulation control that requires only limited calculation, while being extremely flexible and able to very finely adjust stimulation to the observed physical and/or physiological situation.

SUMMARY

More specifically, the disclosure proposes a pacing therapy system, including:
- a stimulation device such as a pulse generator connected to one or more electrodes adapted to be placed on or near a nerve of the autonomic nervous system;
- an external communication device, for communication with the pulse generator;
- at least one sensor of physiological and/or physical signals and processing units of these signals capable of providing at least one current physiological/physical level;
- a control module for controlling the stimulation device according to a set of stimulation parameters; and
- a control module for controlling the stimulation using a transition state model including a transition matrix and a connection matrix, capable of applying optimum stimulation parameters to reduce the current physiological or physical level to a set of given level, the states of the model being characterized by a set of values of stimulation parameters and at least one expected physiological or physical response during stimulation application with these parameters.

In some embodiments, the system includes self-adapting methods of the state transition model, including:

storing the physiological or physical successive levels actually achieved when issuing respective stimulation sets;

adjusting the at least one expected response associated with the set of stimulation parameters, depending on the physiological or physical levels actually achieved upon stimulation with the stimulation parameter set; and ordering the states based on the new values of the characteristic responses.

According to various embodiments:

the new value of the expected physiological or physical response of the model state is calculated from the average of the successive physiological or physical levels recorded during stimulation with the stimulation parameters;

the new value of the expected physiological or physical response from the model state is calculated from the average of the successive current physiological or physical levels and the current value of the expected physiological or physical response;

the new value of the expected physiological or physical response of the model state is calculated from a model of artificial intelligence between the successive current physiological or physical levels and the current value of the expected physiological or physical response;

the self-adaptation of the state transition model is implemented by the external communication device;

the system further can be triggered by an operator, via the external communication device, of known stimulation sequences in the pulse generator, and can transmit successive physiological or physical levels in response to the stimulation sets, to the external communication device. The external communication device includes a control module for: determining new values of the expected physiological or physical response; sorting the states based on the new values of the expected physiological or physical response; and transferring to the pulse generator of the new states with associated pairs {stimulation parameter values, expected physiological or physical response values};

the self-adaptation of the state transition model is made by the pulse generator at predetermined regular intervals (e.g. every cardiac cycle, every hour, every week);

the self-adaptation of the state transition model is implemented by the pulse generator during the occurrence of a predetermined event;

the at least one sensor is a sensor adapted to be integrated in an implantable medical device, and capable of detecting: a cardiac, muscle or nerve electrogram signal; a body, cardiac or muscle, acceleration signal; respiratory bioimpedance, cardiac flow or pressure signal; a temperature signal; and/or a pressure piezometric or cardiac contractility signal;

the physiological and physical level is determined from one of the following physiological or physical variables: heart rate, sinus rhythm variability, blood pressure, cardiac contractility, physical activity, temperature, movement, respiratory rate, or any combination of variables thereof.

BRIEF DESCRIPTION OF THE DRAWINGS

Further features, characteristics and advantages of the present disclosure will become apparent to a person of ordinary skill in the art from the following detailed description of preferred embodiments of the present invention, made with reference to the drawings annexed, in which like reference characters refer to like elements and in which:

FIG. 18 is a flowchart of a learning method based on a population of patients.

FIG. 19 is a simplified flowchart of a learning mechanism specific to a patient.

FIG. 22 illustrates the stimulation parameters for a set of states.

DETAILED DESCRIPTION

We will now describe an embodiment of the device of the disclosure.

A method of the disclosure may be implemented primarily by software using appropriate algorithms automatically and repeatedly executed by a microcontroller or a digital signal processor. For the sake of clarity, the various processing applied are broken down schematically by a number of distinct functional blocks. This representation, however, has only illustrative purpose, these circuits including common elements and corresponding in practice to a plurality of functions generally performed by the same software.

It should be noted at the outset that to the possible extent, the same references are used from one figure to another to designate the same elements.

Figure 1:
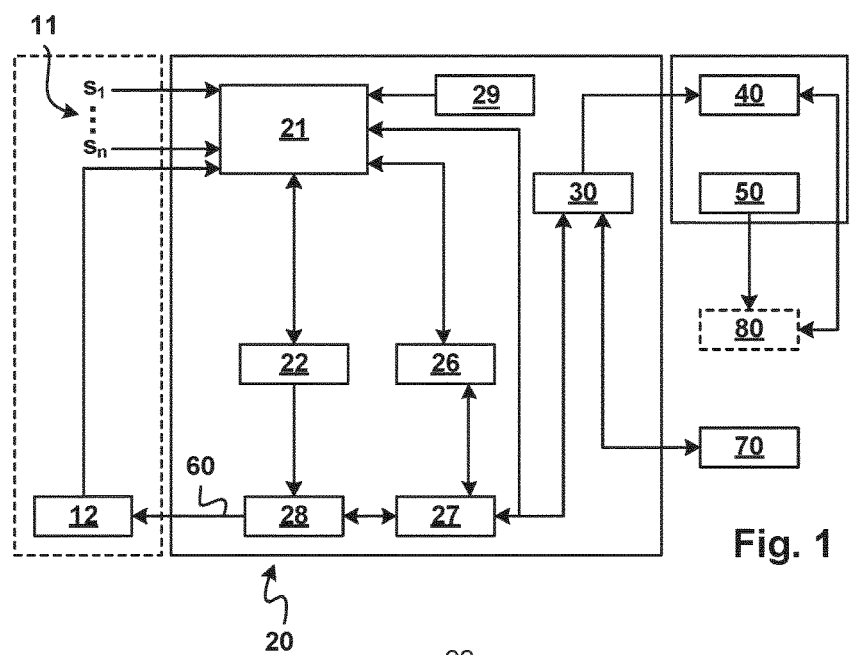
FIG. 1 schematically illustrates the architecture of a closed loop stimulation system.

Referring to FIG. 1, the general architecture of a therapeutic stimulation control system is shown.

Figure 2:
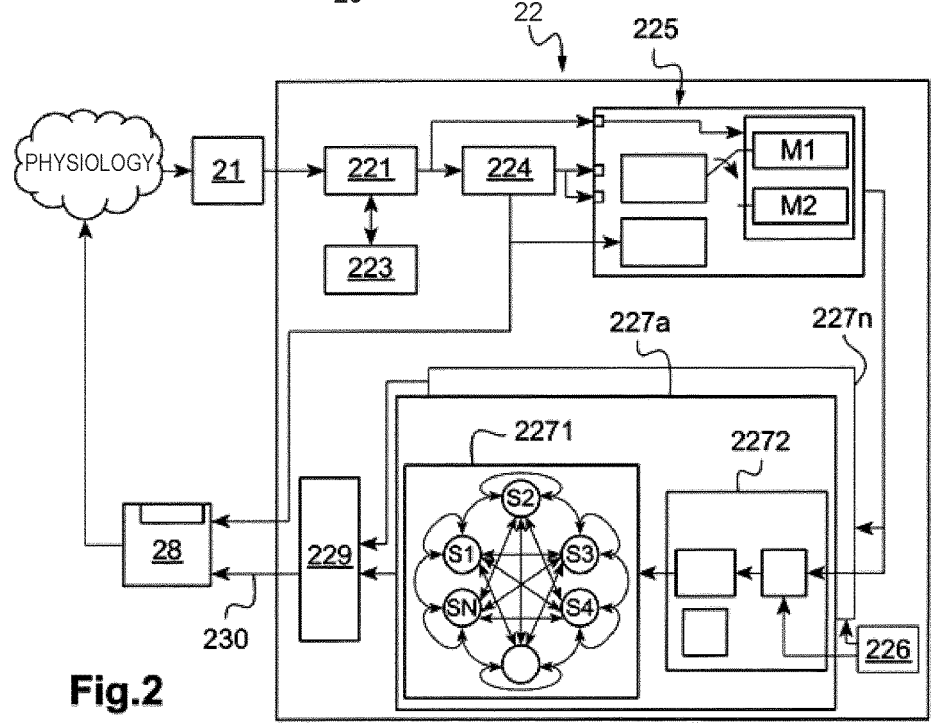
FIG. 2 shows in more detail the architecture of the state transition control system according to an exemplary embodiment.

The device is divided into three major subsystems:

i) an implantable or external pulse generator 20 including the following elements:
- a data processing module in the form of a microcontroller or a microprocessor 27 able to communicate with other modules of the device to receive or send data and control commands;
- a module 21 consisting of a set of sensors and of data processing methods, capable of recording, storing and processing data from the sensors; the data processing methods including but not limited to amplifiers, analog-digital converters, filters, data compressors, and transfer functions;
- a closed-loop control module 22 for dynamically and self-adaptively supplying parameters of optimal stimulation, according to a set of target values for the or each level of physiological or physical variable, hereinafter "PVL" (Physical/Physiological Variable Level); this system will be described below with reference to FIG. 2;
- a memory module 26 capable of storing the operating parameters of the modules 21 (sensor signal acquisition and data processing), 22 (PVL calculation), 27, 28 (stimulator), including desired PVL targets, hereinafter "PVLtarget", for the operation of the control loop, the data calculated in the various modules, and data for clinical monitoring, on different time scales;
- one or more internal sensors 29, for example an accelerometer and/or a temperature sensor;
- a stimulation device 28 applying a stimulation to a physiological structure 12, here the human body; in the examples described below, the device 28 is an electronic module for vagus nerve stimulation; and
- a telemetry module 30 adapted to communicate with an external device such as a programmer 50 or a home remote monitoring device 40, and with another implantable device 70, for example an autonomous lead, an implantable cardioverter defibrillator (ICD) or a cardiac resynchronization therapy device (CRT).

ii) a set 11 of implantable sensors measuring various physiological and physical signals $s_1 \ldots s_n$ of the structure 12, in particular at least one parameter among (but not limited to): minute ventilation, endocardial acceleration (EA), pressure, endocardial electrogram (EGM), or electroneurogram (ENG). These signals are recorded by the module 21 and converted into physiological or physical variables (PVL) such as, but not limited to: heart rate (HR), ventricular contractility, respiratory rate, electroneurogram density, or heart rate variability (HRV). These data can be stored in the memory 26 for analysis on different time scales. Averages of physiological or physical parameters over predetermined durations (for example 1 minute, 24 hours and one week, respectively) can be calculated. For example, an average heart rate over the last 24 hours can be calculated (variable called "meanHR24");

iii) at least one of the following external devices:
- a programmer 50 operating under the physician (or other authorized medical personnel) control 80 and capable of interrogating the pulse generator 20 and of transferring data from the pulse generator to the memory of the programmer, also capable of transferring the programmer setting data to the pulse generator 20, and also capable of viewing reports on screen, in files, database or printer; or
- a home remote monitoring system 40 receiving from the pulse generator 20 certain data and/or alerts to be sent to the physician via a communication system using for example the cellular telephone network and storing them in a database; and iv) an effector 60, for example a vagus nerve stimulation lead, connecting the stimulation module 28 to stimulate to the physiological structure 12.

One embodiment includes closed loop control system, shown in FIG. 2.

Referring to the same figure, the closed loop control system 22 receives as input the signals supplied by the physiological or physical sensors of the module 21, optionally after a preprocessing. In particular, the signals may include ECG signals acquired from an external device, EGM signals provided by a cardiac lead of an implantable device, a pressure, an overall acceleration G, an endocardial acceleration (EA), or ENG signals.

The system 22 also includes a signal processing unit 221, a storage unit 223, an event detection unit 224, a unit 225 for calculating the level of the physical and/or physiological variable PVL, and an interface 226 between the state transition control system 227. The system also includes other modules of the device, such as the memory module 26 of FIG. 1 and which allows, among others, to obtain the target value of the physiological variable (PVLtarget) of the memory 26, and one or more state transition control devices 227a . . . 227n operatively connected in 230 to the neural stimulation unit 28 via a module 229 for parameter fusion, as described below.

Each state transition controller 227 includes two interconnected elements, namely i) a state transition model 2271, containing all the states of the state transition controller and their interconnections, and ii) a calculator 2272 implementing one or more state transition algorithms.

The module 229 of parameter fusion is able to determine the final parameters of neurostimulation as will be described below.

The control device 227 operates in a closed loop configuration. A current physiological and physical variable, hereinafter "PVLcurrent", is measured and preprocessed by 225. The interface 226 contains information for a target value for that physiological variable (PVLtarget). The PVLtarget value can be fixed or dynamic. A fixed PVLtarget can be defined by default in the device, or modified and defined by the expert and stored in memory 26. For example, in the control of the RR interval, the expert can define a PVLtarget=500 ms (fixed) in the memory 26. A dynamic PVLtarget is defined when its value is a function of a measured variable. In this case, the PVLtarget changes over time. For example, in the case of the control of the RR interval, the expert can define a dynamic PVLtarget as a percentage of measured RR (i.e. PVLtarget=10%*PVLcurrent). The calculation of the underlying function of this dynamic definition of PVLtarget is performed in unit 226. Finally, it is important to emphasize that the function used to obtain a dynamic PVLtarget can be any type of mathematical function or a set of logical rules.

Once PVLtarget is defined, an error is calculated in 227 between PVLcurrent and PVLtarget. Finally, on the basis of this error, the control algorithm determines a state transition and the resulting state allows defining the neurostimulation settings.

The state transition controller 227 will now be described. The model of state transition 2271 is composed of a set of N+1 states rated from $S_0$ to $S_N$, where each state corresponds to a set of stimulation parameters and to a set of responses or characteristic effects noted RS.

A state transition model for example is:

$$S_0 = [\, P_{1,0} \quad P_{2,0} \quad \ldots \quad P_{M,0}; RS_{1,0} \quad \ldots \quad RS_{Q,0} \,]$$
$$S_1 = [\, P_{1,1} \quad P_{2,1} \quad \ldots \quad P_{M,1}; RS_{1,1} \quad \ldots \quad RS_{Q,1} \,]$$
$$S_2 = [\, P_{1,2} \quad P_{2,2} \quad \ldots \quad P_{M,2}; RS_{1,2} \quad \ldots \quad RS_{Q,2} \,]$$
$$\ldots$$
$$S_N = [\, P_{1,N} \quad P_{2,N} \quad \ldots \quad P_{M,N}; RS_{1,N} \quad \ldots \quad RS_{Q,N} \,] \quad (1)$$

wherein $S_N$ is the state N, with N=0 . . . N, and is composed of M stimulation parameters of the vagus nerve, denoted $P_{M,N}$. The parameter $P_{M,N}$ may represent any parameter of such a stimulation, for example the number of pulses, the pulse amplitude, pulse width, the pulse frequency, the pacing delay in the case of a neurostimulation synchronous to a physiological event (as cardiac activity), the duty cycle of the pulses, the synchronism of the pulses, etc.

We will consider below an example wherein the state $S_N$ consists of the following:

As stimulation parameters, amplitude, frequency and width of the stimulation pulses;
As characteristic effects, the length of the RR interval of the electrocardiogram and the temporal change (first derivative) of the cardiac pressure.

The five states of the model in this example are the following:

$S_0$=[0 mA 0 Hz 0 µs Baseline Baseline]

$S_1$=[1 mA 64 Hz 120 µs 420 ms 1.90 mmHg/ms]

$S_2$=[2 mA 32 Hz 120 µs 450 ms 2.05 mmHg/ms]

$S_3$=[3 mA 25 Hz 120 µs 500 ms 2.09 mmHg/ms]

$S_4$=[3 mA 12 Hz 240 µs 520 ms 2.15 mmHg/ms] (2)

In each model, one of the states ($S_0$ state) can be configured to stop neurostimulation. This state can be used in all situations where the stimulation is not necessary, even if adverse events (typically cough, pain, arrhythmia, etc.) are detected.

Each state of the state transition model is connected to itself, and can be connected to any other state $S_k$.

Figure 3:
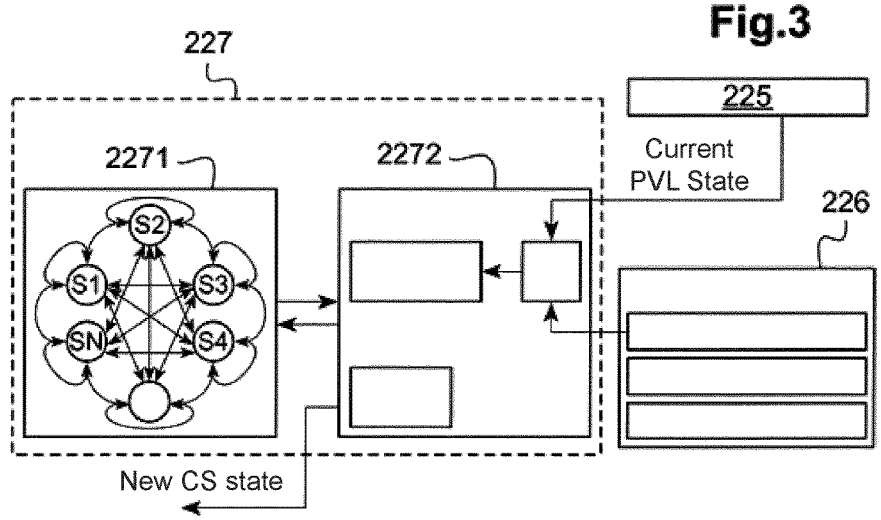
FIG. 3 illustrates in more detail the system and a particular model of state transition.

A particular example illustrated in FIG. 3, is the case of a fully connected state transition model, namely, wherein each state can transit to any other state.

These connections between states, which govern the transitions between states, are defined here in a connection matrix. The connection matrix for a fully connected architecture is illustrated in Table 1 below.

TABLE 1

| State | 0 | 1 | 2 | . . . | $N_k$ |
|---|---|---|---|---|---|
| $S_0$ | 1 | 1 | 1 | 1 | 1 |
| $S_1$ | 1 | 1 | 1 | 1 | 1 |
| $S_2$ | 1 | 1 | 1 | 1 | 1 |
| . . . | 1 | 1 | 1 | 1 | 1 |
| $S_N$ | 1 | 1 | 1 | 1 | 1 |

All cells of the matrix are here to the value 1, meaning that all states can be connected to each other.

The presence of a 0 in a cell of the matrix has the effect of prohibiting direct transition between two states. This can be used as a security measure for prohibiting transitions between specific pacing configurations. For example, in the case of VNS, a too abrupt change in the injected current can cause side effects, and such a change can be avoided by setting a zero value to the corresponding cell(s) the connection matrix.

The state transition calculator is dedicated to the determination of optimal transitions between states, to lead to an optimization of the configuration of the neurostimulation parameters by minimizing the error between the PVLcurrent and PVLtarget.

Transitions between states are defined at specific timings which are here called "events". These events can be scheduled in time (e.g., every minute) or synchronously distributed to a physiological activity (e.g., with each heartbeat), depending on a given situation (for example when the patient is asleep with low variability of the heart rate (HRV)) or any combination of such situations. At each event, the state transition calculator 2272 determines the transition to the most appropriate state, applying a state transition algorithm based on a transition matrix T, described below.

An example of a transition matrix T for a sequential and deterministic transition algorithm is given in Table 2 below.

TABLE 2

| | | t + 1 | | | | | | |
|---|---|---|---|---|---|---|---|---|
| Event | State | 0 | 1 | 2 | 3 | . . . N − 2 | N − 1 | N |
| t | $S_0$ | Cond P | Cond I | | | | | |
| | $S_1$ | Cond P | Cond I | Cond 2 | | | | |
| | $S_2$ | Cond P | Cond 0 | Cond 1 | Cond 2 | 0 | 0 | 0 | 0 |
| | . . . | Cond P | . . . | . . . | . . . | . . . . . . | . . . | . . . |
| | $S_{N-2}$ | Cond P | 0 | 0 | 0 | Cond 1 | Cond 2 | 0 |

TABLE 2-continued

| | | t + 1 | | | | | | |
|---|---|---|---|---|---|---|---|---|
| Event | State | 0 | 1 | 2 | 3 | ... N − 2 | N − 1 | N |
| | $S_{N-1}$ | Cond P | 0 | 0 | 0 | 0 Cond 0 | Cond 1 | Cond 2 |
| | $S_N$ | Cond P | 0 | 0 | 0 | 0 0 | Cond 0 | Cond F |

In this table the state $S_0$ corresponding to the immediate cessation of neurostimulation under certain conditions, for example upon the occurrence of adverse events (typically cough, pain, cardiac arrhythmia, etc.). It is a priority condition (denoted Cond P) which leads to this state, wherein neurostimulation parameters are brought to 0. The condition P has priority over all others.

In addition to this priority status, different conditions may apply. A simplified example of these conditions is:

Condition 1: $PVL_{i,j}$ current≥$PVL_{i,j}$ target

Condition 0: $PVL_{i,j}$ current>$PVL_{i,j}$ target

Condition 1: $PVL_{i,j}$ current=$PVL_{i,j}$ target

Condition 2: $PVL_{i,j}$ current<$PVL_{i,j}$ target

Condition F: $PVL_{i,j}$ current≤$PVL_{i,j}$ target

Condition P: priority condition  (3)

where i and j respectively represent the current state and the future state.

These conditions are given by way of illustrative and simplified example. A person skilled in the art will understand that conditions can be complex, involving combinations of target values and logic operators or function between measured variables.

It should be noted that the transition matrix for the deterministic algorithm includes a set of conditions that may be implemented as rules. The invention also probabilistically processes transitions. In this case, an example of a stochastic transition matrix T may be as follows:

TABLE 3

| | | t + 1 | | | | | | |
|---|---|---|---|---|---|---|---|---|
| Event | State | S1 | S2 | S3 | ... | $S_{N-2}$ | $S_{N-1}$ | $S_N$ |
| t | $S_1$ | $a_{1,1}$ | $a_{1,2}$ | $a_{1,3}$ | $a_{1,...}$ | $a_{1,N-2}$ | $a_{1,N-1}$ | $a_{1,N}$ |
| | $S_2$ | $a_{2,1}$ | $a_{2,2}$ | $a_{2,3}$ | $a_{2,...}$ | $a_{2,N-2}$ | $a_{2,N-1}$ | $a_{2,N}$ |
| | $S_3$ | $a_{3,1}$ | $a_{3,2}$ | $a_{3,3}$ | $a_{3,...}$ | $a_{3,N-2}$ | $a_{3,N-1}$ | $a_{3,N}$ |
| | ... | ... | ... | ... | ... | ... | ... | ... |
| | $S_{N-2}$ | $a_{N-2,1}$ | $a_{N-2,2}$ | $a_{N-2,3}$ | $a_{N-2,...}$ | $a_{N-2,N-2}$ | $a_{N-2,N-1}$ | $a_{N-2,N}$ |
| | $S_{N-1}$ | $a_{N-1,1}$ | $a_{N-1,2}$ | $a_{N-1,3}$ | $a_{N-1,...}$ | $a_{N-1,N-2}$ | $a_{N-1,N-1}$ | $a_{N-1,N}$ |
| | $S_N$ | $a_{N,1}$ | $a_{N,2}$ | $a_{N,3}$ | $a_{N,...}$ | $a_{N,N-2}$ | $a_{N,N-1}$ | $a_{N,N}$ | wherein $$\sum_{j=1}^{N} a_{1,j} = 1, \sum_{j=1}^{N} a_{2,j} = 1, \ldots, \sum_{j=1}^{N} a_{N,j} = 1 \quad (4)$$

and wherein each represents the probability of transition from state i to state j.

Figure 4:
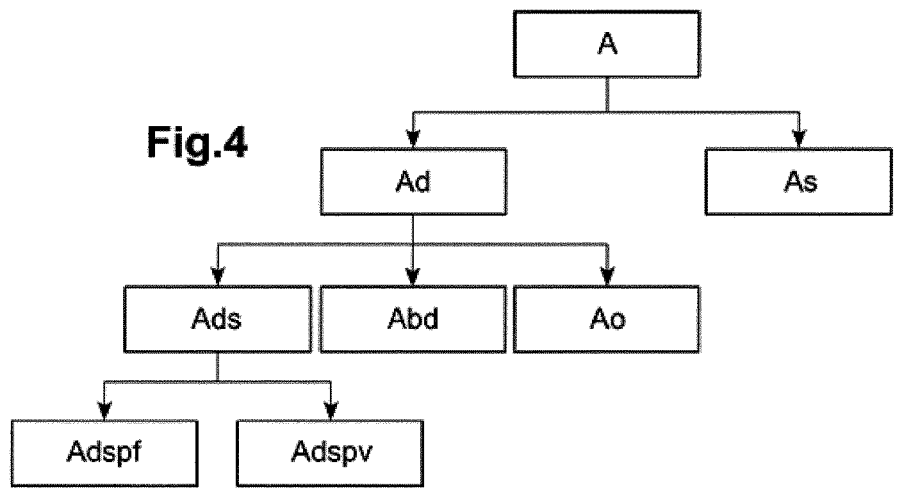
FIG. 4 illustrates various algorithms that can be implemented in a state transition controller.

FIG. 4 shows the hierarchy of a number of examples of transition algorithms A which will be described later, with a stochastic algorithm As, a deterministic algorithm Ad, and in the latter category sequential transition algorithm Ads, which may be with a fixed pitch Adspf or with a variable pitch Adspv, an algorithm based on dichotomy Abd and an optimal algorithm Ao.

An example of a connection matrix C for a sequential state transition algorithm with a stimulation stop state is given in Table 4 below:

TABLE 4

| State | 0 | 1 | 2 | 3 | 4 | ... | N − 1 | N |
|---|---|---|---|---|---|---|---|---|
| $S_0$ | 1 | 1 | 0 | 0 | 0 | 0 | 0 | 0 |
| $S_1$ | 1 | 1 | 1 | 0 | 0 | 0 | 0 | 0 |
| $S_2$ | 1 | 1 | 1 | 1 | 0 | 0 | 0 | 0 |
| $S_3$ | 1 | 0 | 1 | 1 | 1 | 0 | 0 | 0 |
| ... | 1 | — | — | — | — | — | — | — |
| $S_{N-1}$ | 1 | 0 | 0 | 0 | 0 | 1 | 1 | 1 |
| $S_N$ | 1 | 0 | 0 | 0 | 0 | 0 | 1 | 1 |

Figure 5:
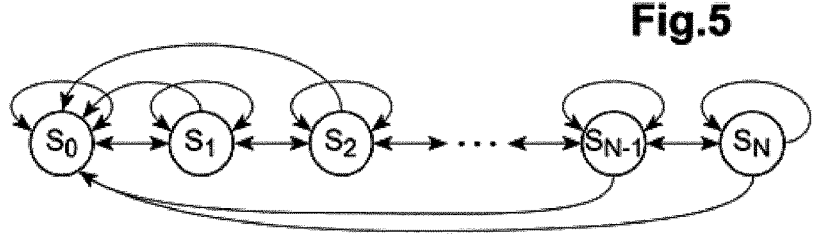
FIG. 5 graphically illustrates a particular mode of transition between states.

From this table it can be seen that each state of the state transition model is connected to $S_0$, to itself and to its adjacent states, as shown in FIG. 5.

The state $S_0$ corresponds to an immediate cessation of neurostimulation in the case of adverse events, as described above.

In one embodiment, the states of the state transition model are categorized depending on the effect they cause on or physiological variables to control. The states $S_0$ to $S_4$ given above by way of example (2) are an example of categorized states vis-a-vis the regulation of the RR interval and of the temporal change (first derivative) of the cardiac pressure.

Figure 6:
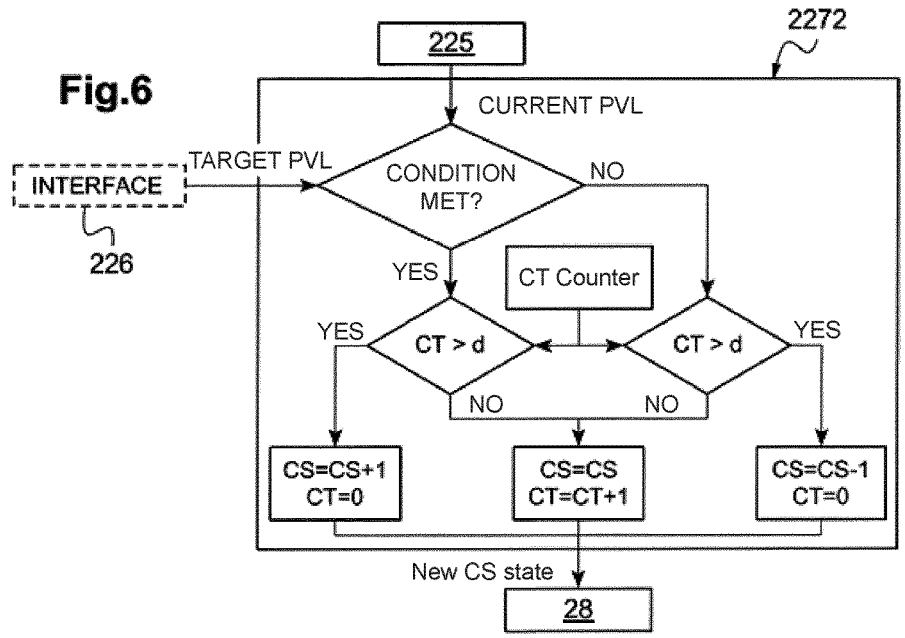
FIG. 6 shows the architecture of a deterministic and sequential state transition controller with fixed pitch.

An example of deterministic and sequential state transition algorithm with fixed step Adspf is illustrated in FIG. 6.

In this case, the step of 1 corresponds to the transition from a state i to a state j immediately adjacent. The counter (CT) enables updating the state every d events, e.g. every 5 cardiac cycles.

Figure 7:
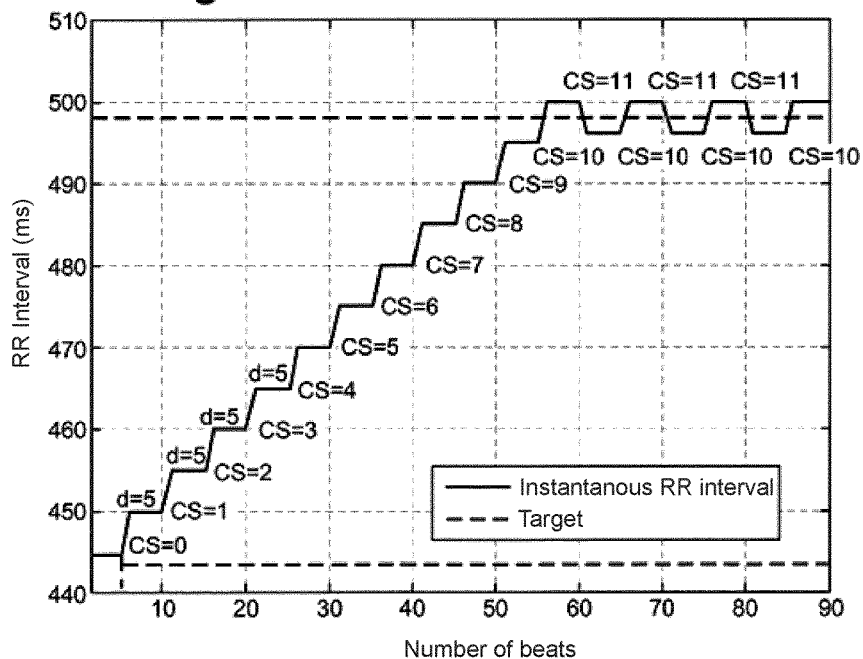
FIG. 7 illustrates the current state changes in response to the action of this controller.

An example of the method by which this algorithm may operate for regulating the instantaneous RR interval of a patient is illustrated in FIG. 7. In this example, the target value of the RR interval is set to 498 ms and the value is set at 5 cardiac cycles.

The same figure shows that the current state (CS) increases every 5 beats until the observed value of the RR interval is greater than the target value (CS=11). Then, the CS current state oscillates between CS=11 and CS=10 values. The oscillation period is 5 beats.

Figure 8:
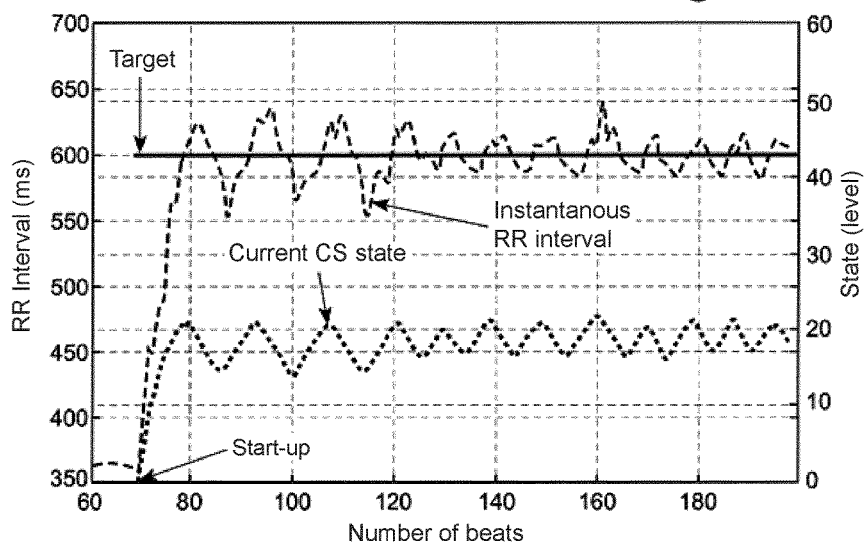
FIG. 8 illustrates another mode of current state change and the corresponding appearance of a real physiological level relative to a target physiological level.

In a real preclinical recording, the result of the application of the algorithm is shown in FIG. 8. The target value of the RR interval is set at 600 ms and d=4 cardiac cycles. It can be seen that the target value of the RR interval is reached.

The advantages of the algorithm Adspf are that the target value can be achieved with good accuracy and the transition algorithm is simple.

Figure 9:
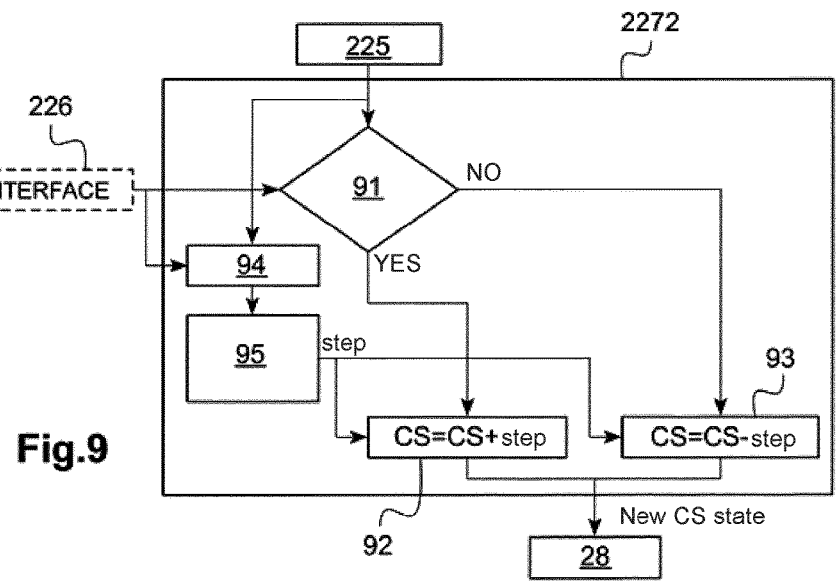
FIG. 9 illustrates the architecture of a deterministic and sequential state transition controller with variable pitch.

A more sophisticated version of the sequential deterministic algorithm Ads is illustrated in FIG. 9.

With this algorithm, if the condition of the control device is met (for example if the PVLcurrent value is less than the value of PVLtarget, box 91), then the algorithm executes (box 92) CS=CS+step. Otherwise, the algorithm executes (box 93) CS=CS−step. In this case, the step value, which is updated at each event, depends on the amplitude of the error, that is:

$$e=\text{PVLtarget}=\text{PVL current}$$

$$\text{Step}=f(e)$$

calculated at the box 94.

The box 95 determines the value of the step. Generally, the higher the value of e, then the higher the value of the step is. Conversely, the smaller the value of e, the smaller the step value is. In some embodiments, the step value may result from the application of a nonlinear function on the error value e (e.g., sigmoid); in other embodiments, the step value may result from the application of a linear function on the value of the error e confined to the minimum and maximum step limits.

The benefits of this implementation are that the goal is usually achieved with precision, and it is faster than the algorithms described above.

An embodiment with a deterministic transition algorithm based on the Abd dichotomy will now be described. In this case, the state transition computer 2272 operates according to a dichotomous principle, as illustrated in FIG. 10.

In this figure, two registers $CS_{max}$ and $CS_{min}$ are initialized with $CS_{max}$=N and $CS_{min}$=0. The current state CS is set to the value $CS=(CS_{max}-CS_{min})/2$ (box 101). When the control system is initiated, the stimulation device delivers stimulation. Then the new value of PVLcurrent, which has already been affected by the stimulation, is calculated from the collected signals. If the condition of the control device (box 102) is met (e.g. if the measured value (PVLcurrent) is less than the value of PVLtarget), then the $CS_{min}$ variable is updated, namely $CS_{min}$=CS, and the current state CS is calculated with $CS=CS_{min}+(CS_{max}-CS_{min})/2$ (box 103). Otherwise, the $CS_{max}$ variable is updated, namely $CS_{max}$=CS, and the current state is calculated with $CS=CS_{min}+(CS_{max}-CS_{min})/2$ (box 104).

Figure 10:
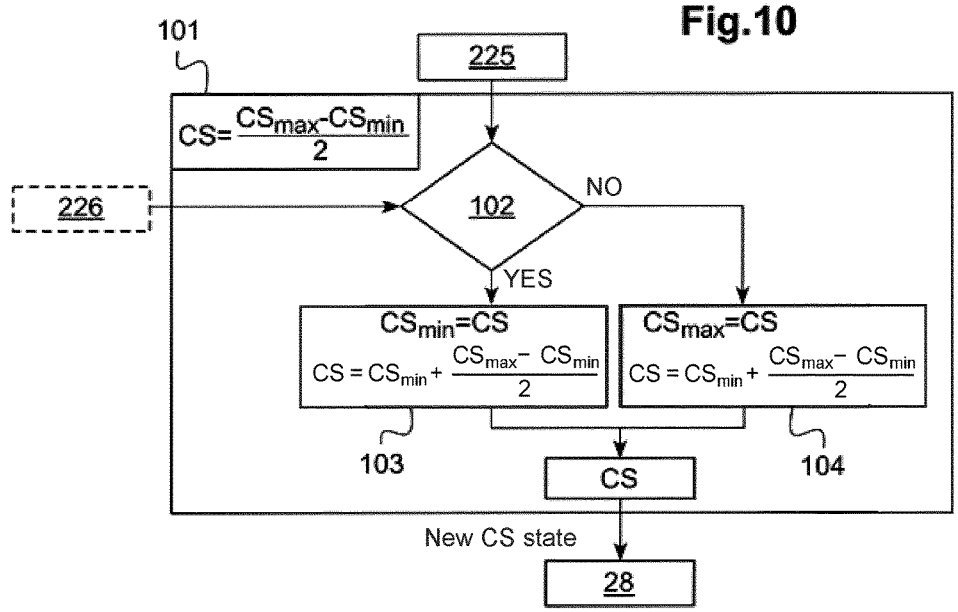
FIG. 10 illustrates the architecture of a deterministic state transition controller with dichotomous basis.

In the algorithm shown in FIG. 10, the following condition (not shown) must be taken into account: if $CS=CS_{min}+(CS_{max}-CS_{min})/2$ is not an integer, then CS must be rounded to the nearest integer value.

The advantages of such a dichotomous based algorithm are achieving the target accurately, and in general, with greater speed than the algorithms described above.

Figure 10A:
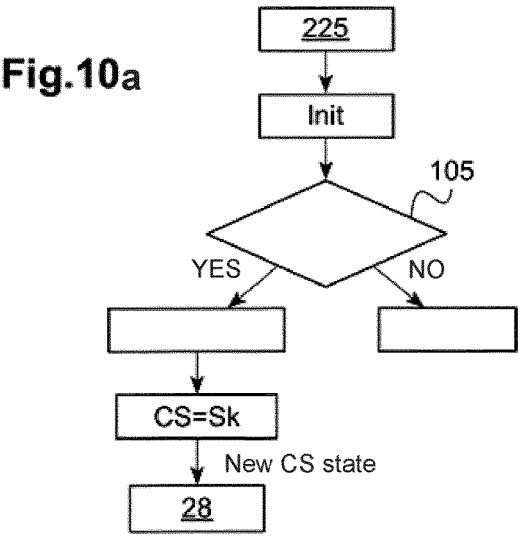
FIG. 10a shows the architecture of an optimized deterministic state transition controller.

An embodiment of an optimal deterministic state transition algorithm Ao will now be described with reference to FIG. 10a. In this embodiment, the 2272 state transition calculator uses an expected response value RS previously stored in the 2271 state transition model (it is recalled here that in various embodiments, each state transition model 601 contains the state or the expected answers for the parameters of the state, see list (1) above).

In this approach, when a target PVL value is set, the state transition calculator 2272 researches the expected minimum response RS for which the following condition of the control device:

$$\text{error}(\text{PVLtarget},\text{PVLcurrent})>\text{threshold}CL$$

(tested in box 105) is met and wherein thresholdCL is defined by an expert.

If so, this means that the current state CS is the state containing the value of RS.

For example, let us assume that one uses here the state transition model with four active states listed in (2) above, namely:

$S_1$=[1 mA 64 Hz 120 μs 420 ms 1.90 mmHg/ms]

$S_2$=[2 mA 32 Hz 120 μs 440 ms 2.05 mmHg/ms]

$S_3$=[3 mA 25 Hz 120 μs 500 ms 2.09 mmHg/ms]

$S_4$=[3 mA 12 Hz 240 μs 520 ms 2.15 mmHg/ms]

Let us suppose now that we are interested in the regulation of the RR interval to a target value of 440 ms. The transition algorithm will then select $S_2$ as the current state, because this state $S_2$ is the lowest value that meets the condition:

$$RS>\text{PVLtarget}.$$

As previously described a $S_0$ state can be used for security.

An advantage of this algorithm is that the objective is usually achieved with precision, and faster than with the algorithms previously described.

It will be noted here that the connection matrix C as shown in Table 1 can be used with the deterministic and sequential variable step Adspv transition algorithm, with the dichotomous basis Abd deterministic transition algorithm and with the optimal deterministic transition algorithm Ao.

An embodiment using a stochastic transition algorithm As will now be described.

While the optimal deterministic approach described above is based on the assumption that a given stimulation configuration Pi always generates the exact expected response RSi, this generally not true in physiology due to the complexity of these systems.

A stochastic approach according to this embodiment aims to treat some of the uncertainty associated with this complexity by applying a transition probability in a given state.

In all embodiments of the state transition calculator 2272 operating according to probabilistic laws, probabilistic graphs can be used to calculate the state transition to select from the state transition model.

A probability graph is a directed and weighted graph for which:

There is at least an arc from one state to another or to itself.

The sum of the weights of the arcs from the same state is 1 (Equation 4).

Note that the weights are then probabilities, namely real numbers between 0 and 1 and that a probability graph shows the possible states of the system and the transition probabilities from one state to another (arc weight).

Figure 11:
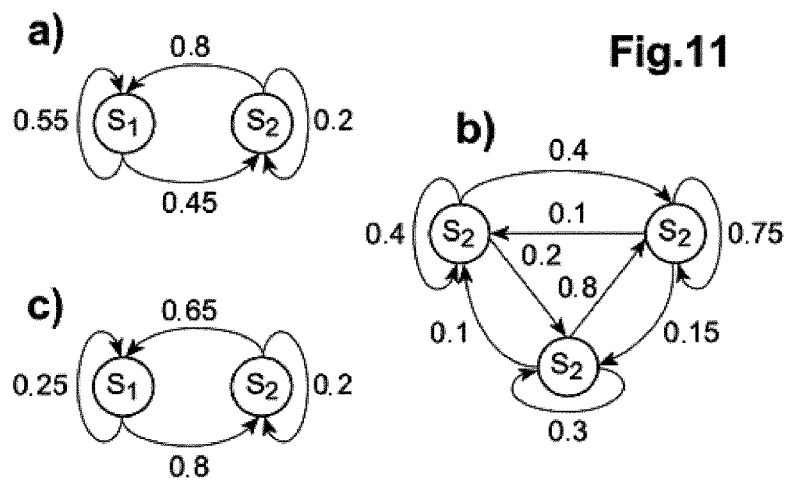
FIG. 11 shows transitions between states controlled by a stochastic transition model.

FIG. 11a is an example of probabilistic graph of order two (two states). FIG. 11b is an example of a probabilistic graph of order three. FIG. 11c shows an example of a non-probabilistic graph, since the sum of the weights of arcs leaving the state $S_1$ is 1.05, not 1.

In one embodiment, a Markov matrix is used to determine the optimal transitions to achieve the target level of the physiological variable, as described in Table 3, wherein is the probability of a transition from one state to another in the state transition model.

As described above, a state $S_0$ can be provided for emergency control conditions.

In one embodiment, the probabilities $a_{i,j}$ are calculated during a learning phase, via hidden Markov model algorithms (HMM, Hidden Markov Model). For example, after setting the number of states, the Baum-Welch algorithm (forward-backward) allows to estimate all parameters of the transition state model (HMM here) iteratively, from a learning database. Other algorithms, such as the Iterated Conditional Estimator may also be used. Once these parameters are identified, from a sequence of observations, the Viterbi algorithm calculates the state sequence that most likely corresponds, while the forward algorithm calculates the probability of a particular sequence of observations.

Figure 12:
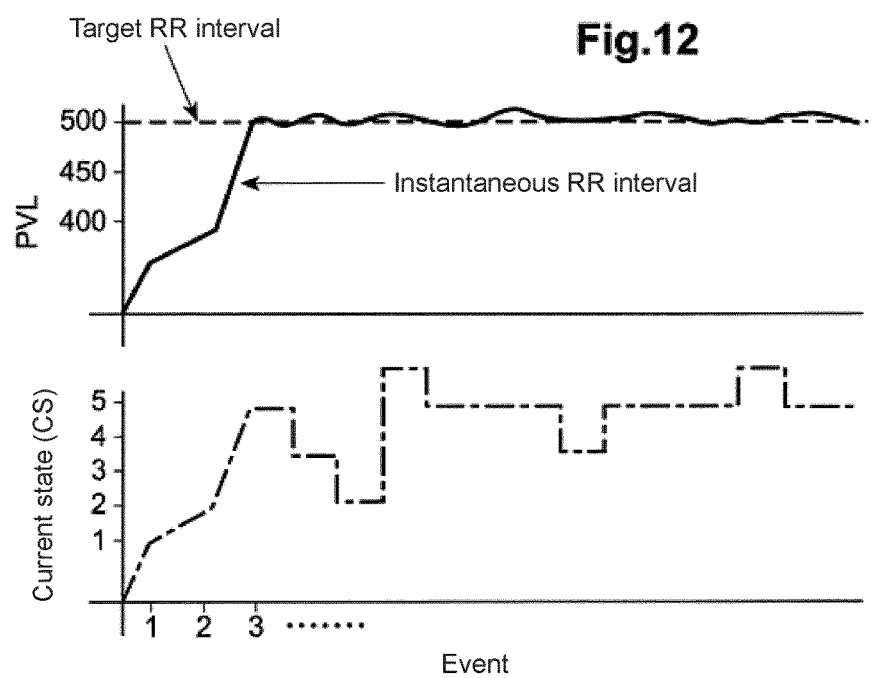
FIG. 12 shows the evolution of states and the evolution of the real physiological level compared to a target physiological level with the stochastic model.

An example diagram of the effect of this transition algorithm is illustrated in FIG. 12. The target value of the RR interval is set at 500 ms. A state transition model (HMM) with N states with N=10 is used. It is observed that the transition algorithm leads to states $CS=S_3$ and $CS=S_2$ and leads directly to the state $CS=S_5$, which here, depending on conditions, is able to better drive the level of the physiological variable to its target value.

In this example, there are no particular rules as in the deterministic algorithms. In this example, the transitions are based on probabilities associated with the transition matrix T. It is further observed that the states may vary in a probabilistic method, even if the target physiological value remains constant. This probabilistic behavior can be particularly important in physiological and clinical applications because the underlying processes are complex and therefore have a natural variability that can be represented by a random process.

An embodiment with closed-loop control with variable temporal resolution will now be described.

Adaptive neurostimulation devices should be able to adapt the therapy to both variables likely to change quickly (time scale of seconds or minute) and variables likely to change slowly (scale time of day, month, year). In this embodiment, for example, two time scales are used:

- physiological variables with quick changes are often variables controlled in the short term by the autonomic nervous system, such as heart rate, blood pressure, contractility, etc. They are linked to changes in patient activity or acute worsening of the patient's condition (e.g. myocardial infarction); other short-term variables are related to the occurrence of adverse events (cough, contraction of the neck muscles, etc.). These variables require an immediate reaction, such as an interruption of neurostimulation;
- physiological variables with slow changes or with long-term dynamic are linked to:
- slow physiological mechanisms, corresponding to an improvement or a deterioration in the patient's condition, such as the modification of cardiac hemodynamic performance, resulting in gain changes of autonomous channels; they can be assessed in particular by the average heart rate, changes in heart rate variability (HRV), or a change in the sympathovagal balance (SVB), but also by the patient's mean activity, by the measure by a accelerometer, among others;
- electromechanical phenomena, such as changes in coupling between the electrode and the nerve due to progressive fibrosis, usually after the introduction of the stimulation electrode.

Neurostimulation therapy is adapted to track these changes at different temporal resolutions.

Figure 13:
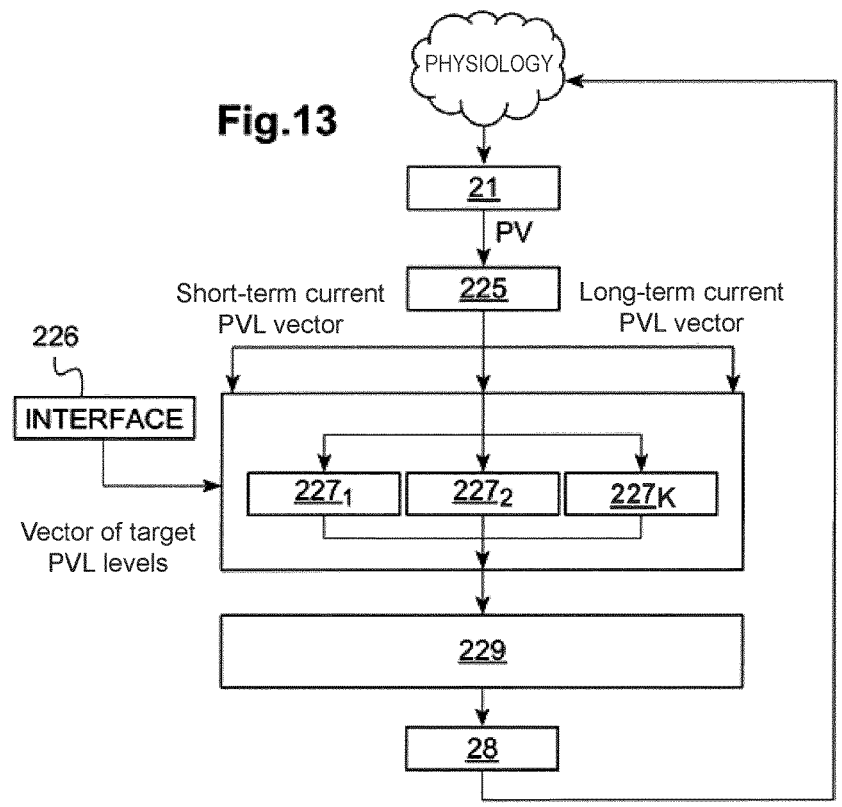
FIG. 13 illustrates the architecture of a state transition controller with multiple temporal resolutions.

Temporal multiresolution is provided in this embodiment, as shown in FIG. 13, by providing a plurality of state transition control devices, respectively $227_1, 227_2 \ldots 227_K$, each device operating with a different temporal resolution and with different parameters of the state transition model and with different algorithms, as defined above.

To illustrate this feature, we will describe a version of the control system incorporating K state transition control devices, here with K=2.

Thus the control system is composed of two transition control devices $227_1$ and $227_2$ state, one ensuring a regulation of a physiological variable in the short term (denoted by PV1) and the other providing a regulation of a physiological variable in the long run (denoted PV2), and changes in this variable PV2 affecting the effect of vagus nerve stimulation (VNS) on the PV1 variable.

Figure 14:
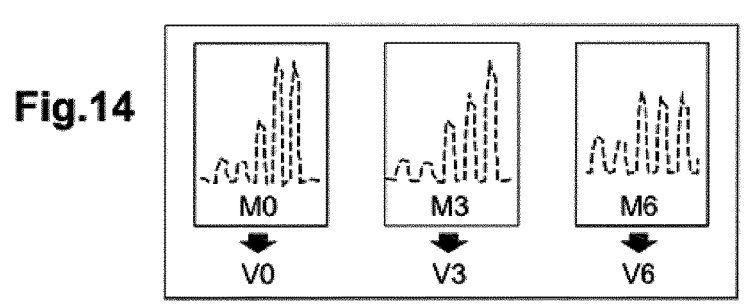
FIG. 14 illustrates different responses to the same stimulus in response to physiological changes in the long term, at spaced moments also in the long term.

In such circumstances, the effect of a given VNS stimulation may change over time, as illustrated in FIG. 14. In this Figure, M0 shows the effect of VNS stimulation on the PV1 variable during implantation, M3 shows the effect of VNS on the PV1 variable three months after implantation, and M6 represents the effect of VNS stimulation on the PV1 variable six months after implantation. The three curves shown in FIG. 14 were obtained with the same five configurations of successive VNS stimulation parameters.

In this example, a first control device is used to regulate the variable PV1, while the second control device estimates the effect of stimulation on the variable PV1 and compensates for variations in this effect on the M0, M3, M6 time scale.

Figure 15:
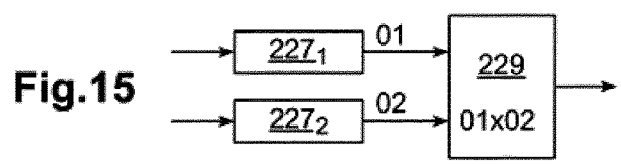
FIG. 15 shows a combination (or fusion) of state transition instructions given by the two transition controllers of different states of the same system.

FIG. 15 shows an example of the method by which the control system can be implemented, the control devices $227_1, 227_2$ issuing instructions 01 and 02 which are merged at the merging module 229 to determine the current state to which to transition.

In this example, this fusion is a multiplication.

Figure 16:
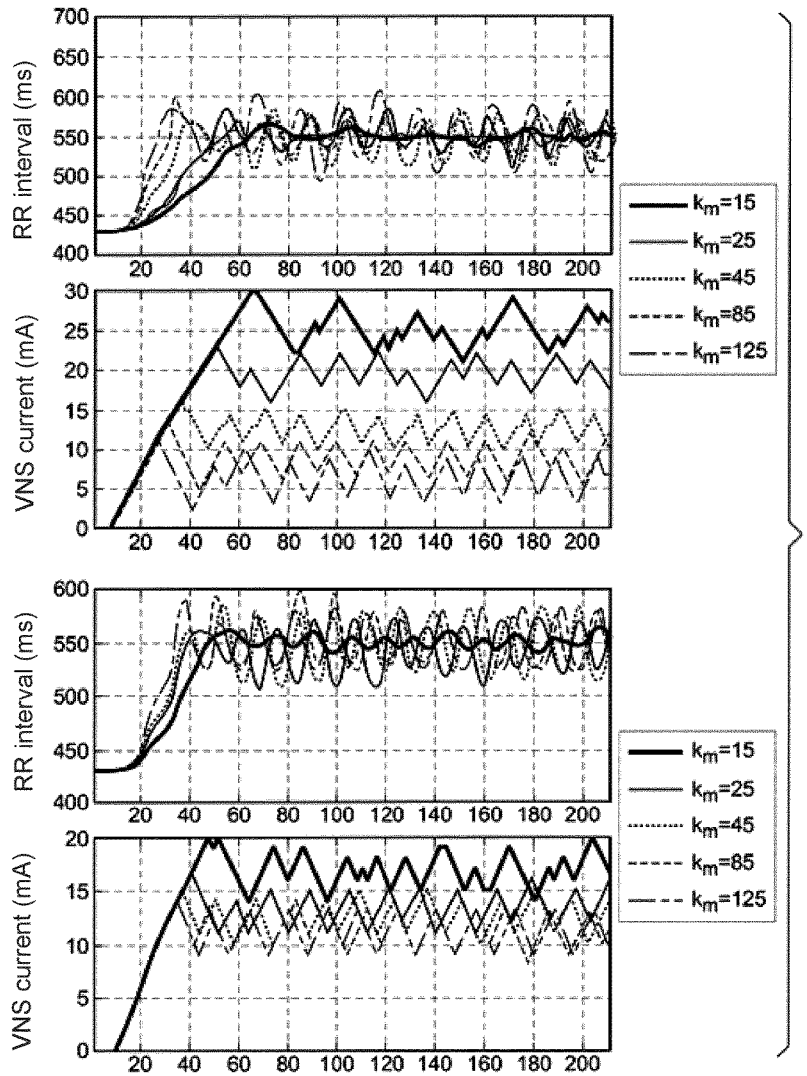
FIG. 16 comparatively illustrates the behaviors of responses to state changes respectively with only one state transition controller in the short term and with two state transition controllers respectively in the short term and in the long term.

FIG. 16a shows in the upper part the response of the variable PV1 when a single control device is used. FIG. 16b shows in the upper part the response of the variable PV1 when two control devices are used. The different curves correspond to different moments (by month, day, year or other) to which a PVLtarget value of the physiological variable PV1 is established.

It is observed down in FIG. 16a that when a single controller is used, the output of the control device $227_1$ leads to different stimulation parameters to achieve the target. This is explained by the impact of changes in variable PV2 on the effect of VNS stimulation on the PV1 variable.

On the contrary, as shown at the bottom of FIG. 16b, when two control devices $227_1, 227_2$ are used. The output of the $227_1$ control device leads to stimulation parameters with similar values to achieve the target, due to the compensation ensured by the second controller $227_2$. The approach with two control devices provides better accuracy and lower convergence time, while using a simpler transition state model (lower number of states).

A special case of control with a plurality of control devices is when one or more models of probabilistic transition states are used to improve the accuracy around an area of values of the PVLtarget and one or more models of deterministic transition states are used to improve the convergence speed (time required to reach the target). In this case, each control device will have a different probabilistic or deterministic model and the fusion module 229 will set the final stimulation parameters.

Algorithms with a learning phase will now be described.

Different patients may respond differently to the same VNS stimulation configuration. Therefore, a VNS therapy (i.e. the various stimulation parameters and therefore, different possible states of the transition state model) is adapted during a learning phase specific to the patient. This learning phase can be time consuming, and in some cases it may be difficult to implement it.

In such cases, a generalized VNS stimulation configuration is used (as a general state table), derived from analysis of a database of a population similar to that of the patient being treated.

In a more sophisticated embodiment, this general state table may be used as an initial state table, and a learning phase specific to the patient may be constructed to improve the accuracy of the control system.

This embodiment is advantageously based on a closed loop approach that integrates patient-specific properties.

To implement the state transition control device(s), the main parameters of the associated state transition model from population data, or specifically to the patient are identified.

Figure 17:
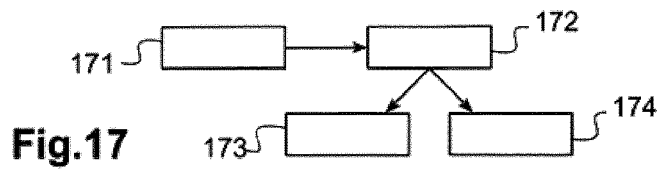
FIG. 17 illustrates different possibilities of a learning mechanism for a state transition controller.

Referring to FIG. 17, the architecture of the controller and the parameters of the state transition models, mainly the matrices C and T, are defined (step 171) by implementing a learning phase 172, which may be based on a population (step 173) or be specific to the patient (step 174).

The structure of each state transition control device is characterized by the definition of the number of states of the model and the desired interstate connections (as defined in the matrix C). These definitions are set from an analysis of the needs. Once this structure is defined, the parameters of the state transition algorithm (mainly the set of stimulation parameters $P_{Mk,Nk,k}$ and the achieved values $RS_{Qk,Nk,k}$ for each state, and the transition matrix T, must be determined.

In general, the learning phase consists of stimulating the patient (or several patients) with a set of stimulation parameters and to analyze the values of physiological variables reached with these parameter sets. From these observations, an analysis is performed to define the structure and parameters of each state transition model and in particular the matrices C and T. In addition, this learning phase can detect parameters that have side effects, so as to exclude them from the state transition model.

A learning phase based on the population is illustrated in FIG. 18. This approach is based on the analysis of a population database, typically characteristic of the pathology in question, including records of interesting physiological variables, for different patients, and with different stimulation parameters for each patient. The $P_{Mk,Nk,k}$ parameters and the achieved values $RS_{Qk,Nk,k}$ for each state (constituting the $S_{nk,k}$ set) and the matrix T are obtained by sensitive analysis on the available data. FIG. 18 illustrates the complete flow-chart of this learning phase based on population.

As mentioned above, the parameters that are likely to cause side effects are not used in the state transition model (see adverse effects test of FIG. 18).

The block diagram of a learning phase specific to the patient is illustrated in FIG. 19.

In order to evaluate the effect of each set of stimulation parameters ($S_{nk}$) on the physiological variables PVLs of a particular patient, this learning method specific to the patient can be applied in a intraoperative or postoperative session, typically during monitoring visits. In this method, the patient is stimulated using a set of stimulation parameters, with a scan of the parameter values, and the effect on PVL variables (or on a primary variable at stake) is measured. The $P_{Mk,Nk,k}$ settings and the achieved values $RS_{Qk,Nk,k}$ for each state (constituting the $S_{nk,k}$ set) as well as the matrix T, are obtained by analyzing the data.

Again, the settings that are likely to cause adverse effects are not used in the state transition model.

Figure 20:
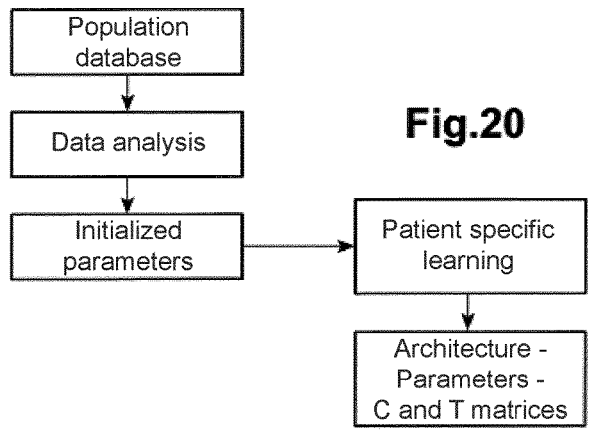
FIG. 20 is a simplified flow diagram illustrating the combination of learning based on a population of patients and of learning specific to a patient.

It is possible to combine the approaches mentioned above (i) by beginning with a definition of parameters based on the population and (ii) by fine-tuning these settings during an intraoperative and/or postoperative analysis session as illustrated in FIG. 20.

Figure 21:
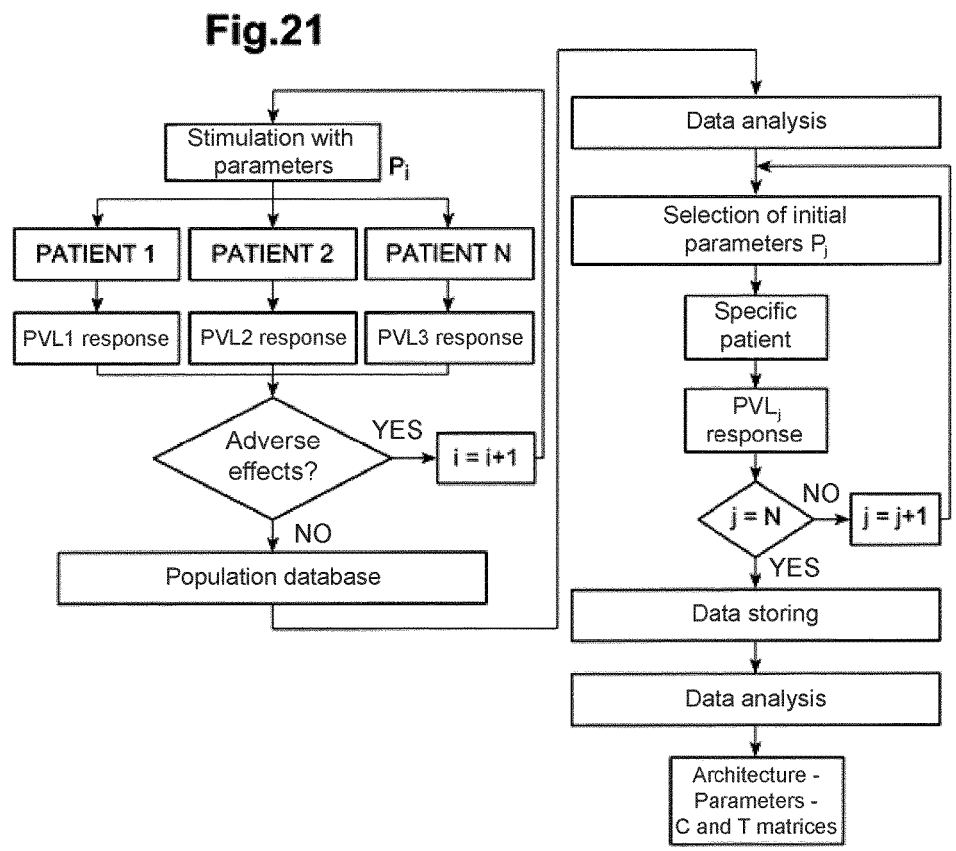
FIG. 21 is a detailed flow chart of the combination of learning of FIG. 20.

A full program of this combined learning method is illustrated in FIG. 21.

It is noted that these learning approaches can be implemented for each K state transition control device, in an arrangement with several control devices.

Upon completion of this learning phase, all parameters are stored in the memory 223 of the stimulation device and the deterministic, stochastic or combined as described above, control algorithm can begin to operate on the basis of these settings.

Figure 23:
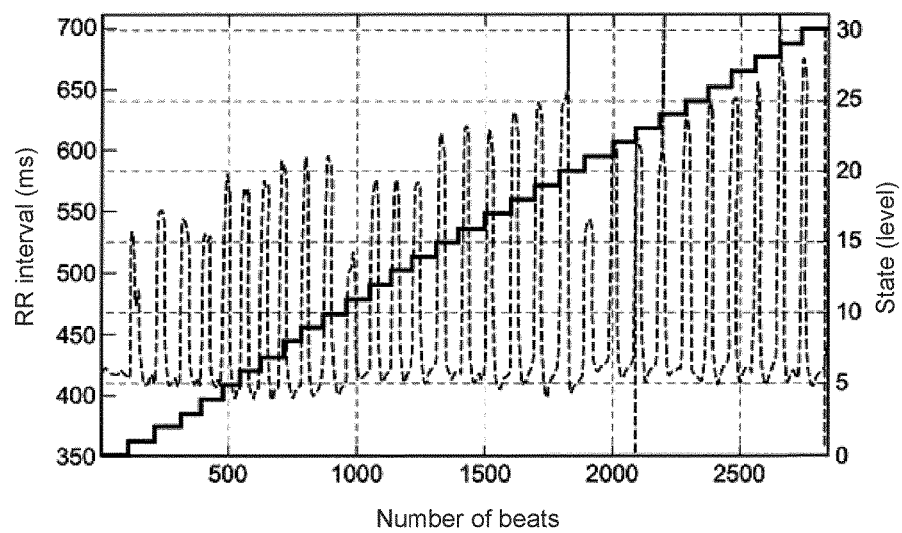
FIG. 23 is a graph showing changes over time of a physiological level and the corresponding state transitions.

An example of a learning phase applied to an animal model will now be described:
1) Initialization (FIG. 22): the state transition model is initialized with the stimulation parameters from the analysis of a population database; on this FIG. 22, the first column indicates the number N of vagus nerve stimulation pulses VNS, the second column indicates the pulse period in ms, and the third column indicates the pulse amplitude (in the form of current pulse expressed in mA);
2) Learning (FIG. 23): the vagus nerve is stimulated using each VNS parameter set of the initialized state transition model. At the same time, the expected value of PVL ($RS_{Qk,Nk,k}$) corresponding to each set of VNS parameters ($P_{Mk,Nk,k}$) is associated with the corresponding state. In this particular example, each VNS stimulation pattern is applied for 15 seconds and the average value of the RR interval ($RR_{stim}$) is calculated from the last five beats; a rest period (absence of stimulation for 45 seconds) allows the RR interval to return to baseline ($RR_{rest}$); and the changes in the RR interval, denoted $\Delta RR$, are calculated from the following equation:

$$\Delta RR = 100 \times \frac{RR_{rest} - RR_{stim}}{RR_{rest}}$$

where:

$$RR_{stim} = \frac{1}{N-5+1} \sum_{i=5}^{N} RR_i$$

$$RR_{rest} = \frac{1}{4} \sum_{i=1}^{4} RR_i$$

Figure 24:
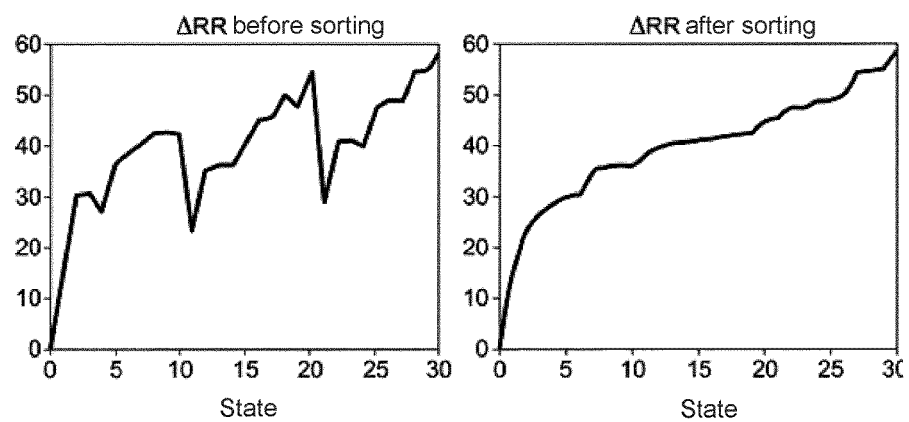
FIG. 24 shows gaps of physiological levels, representing the effect of the stimulation using the associated settings with each state, respectively before and after sorting of states in relation to the effect.

3) Sorting of parameters: after learning the parameters of the VNS stimulation are sorted in ascending order, based on $\Delta RR$ values (see FIG. 24: start from left before sorting, right side after sorting). It is important to emphasize here that a step of state fusion may be realized at that stage. For example, if two consecutive states (after sorting) cause similar effects (states 15 and 16 of the after sorting graph of FIG. 24), only one of these states may be retained and thus reduce the number of global transition model states.

Note that the phases of learning and sorting are used to maximize smooth operation of the deterministic and sequential state transition algorithm, since such an algorithm is based on the principle that the effect measured from each current stimulation state (CS) is as greater as the level of stimulation of the current state in question is important.

An adaptive stimulation system will now be described, realizing an update of the control system parameters over time.

The settings defined for each control device at the beginning of therapy may be suboptimal at a later time, because the physiological and physical condition of the patient is constantly changing due to various predictable factors such as the seasonal and circadian rhythms, or unpredictable factors as the environmental changes (temperature, sociality, etc.), chronic or acute diseases (seasonal influenza, cancer, heart failure, etc.), behavior (diet, activity, alcohol consumption, smoking, etc.), adverse events, etc.

In order to provide optimal therapy, the evolution of the patient's condition may require regular update of the key parameters of the state transition model. This is what allows the method of adaptive parameter estimation proposed here, which can further be applied to different temporal resolutions, for example every day, once a week, once a month, etc. This update of the control device settings can also be implemented based on patient activity (exercise, sleep, etc.). Thus, by implementing this adaptive approach, it is possible to avoid or reduce medical visits and permanently issue optimal therapy.

Each time the patient is stimulated with a given set of parameters, the implantable device obtains the actual effect on the patient using the computer 225 of the physiological variable level. This effect is believed to be close to the expected value RSi.

However, due to the intra-patient variability, the progression of a disease and the effect of the therapy, these values may be significantly different. When the difference between these values exceeds a threshold noted PVL_THRES, it may be decided (i) to record this event as element of the system analysis and (ii) to enable an adaptive algorithm that updates the settings of the control device.

Figure 25:
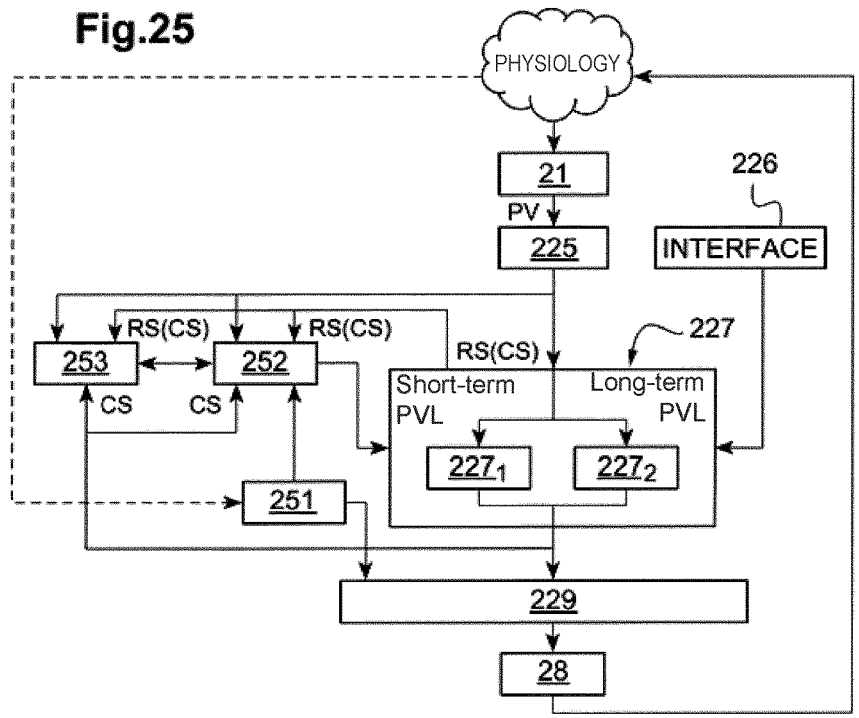
FIG. 25 illustrates the architecture of an adaptive state transition controller system.

FIG. 25 illustrates in detail the architecture of the adaptive configuration. In this figure and as described above, the PV values measurements delivered by the unit 21 are used to calculate different physiological value levels PVL using the PVL level computer 225 (for example and not limited to the interval RR, the maximum peak variation of the recorded blood pressure $(dP/dt)_{max}$, and/or physical activity). These variables are introduced into the proposed control system, consisting of one or more state transition control devices, here two devices $227_1$ and $227_2$.

Each state transition control device generates a set of possible parameters depending on the level PVL received from the controller. An activity sensor module 251 detects the patient activity during the day, for example by describing it on different "rest", "walk", "sleep", "food" levels. This activity information is used by a parameter reconfiguration module 252 implementing a dedicated reconfiguration algorithm and by the module 229 of management of the fusion parameters to adapt the state transition model and the therapy to the patient's activity.

The parameter fusion management module selects the optimal set of VNS stimulation parameters from a series of possible sets of parameters to achieve short-term and long-term physiological targets. It may be decided that in certain patient activity levels, VNS is not issued ($S_0$ state), for example during the "sleep".

The patient is then stimulated with this set of parameters. An analysis module 253 and the parameter reconfiguration module receive the current state CS (setting the current data set) and the level of the physiological variable PVL obtained with this state and determine if the state transition model must be reconfigured or not.

An advantage of this adaptive approach lies in that the analysis module and the parameters reconfiguration module are adapted to detect the parameter settings (states) causing side effects. If a state causes side effects (this effect can be previously detected by the available sensors), then the parameter reconfiguration module may reject this state (making it unavailable), or modify the VNS parameter values of this state.

The parameter configuration module 252 adapts the state transition model if necessary, by approaches such as that described below.

Figure 26:
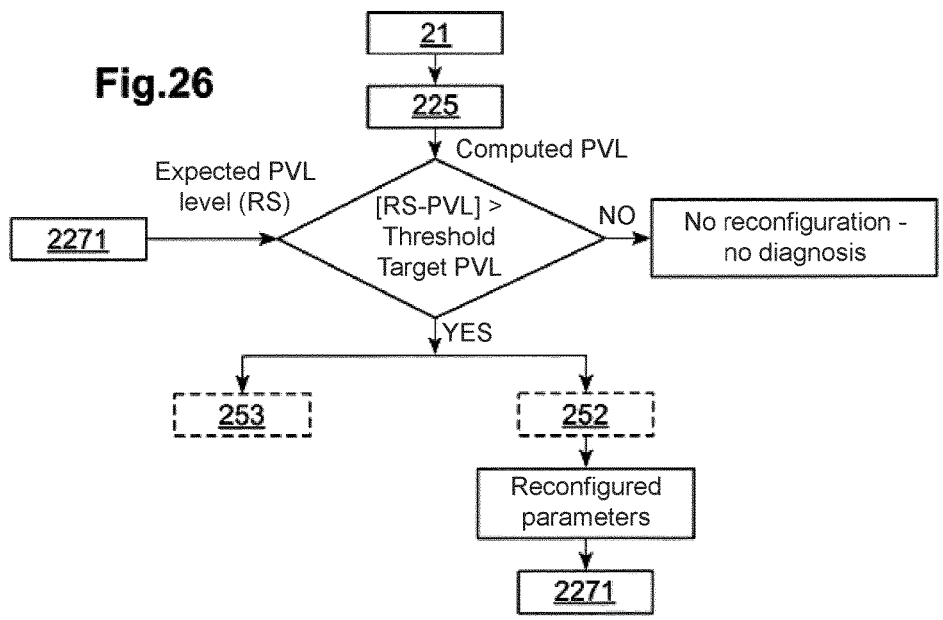
FIG. 26 is a flowchart of the adaptive controller of FIG. 25.

Another application of this adaptive approach may include the activation of pre-programmed VNS stimulation protocols, leading to an update of the expected responses for each state ($RS_{Qk,Nk,k}$), either regularly over time, or at the occurrence of any specified event, as described below. FIG. 26 shows the flowchart of the proposed adaptive approach.

Various embodiments of this adaptive approach will now be described.

Recall that the adaptation of the state transition model is advantageously carried out with different temporal resolutions.

Figure 27:
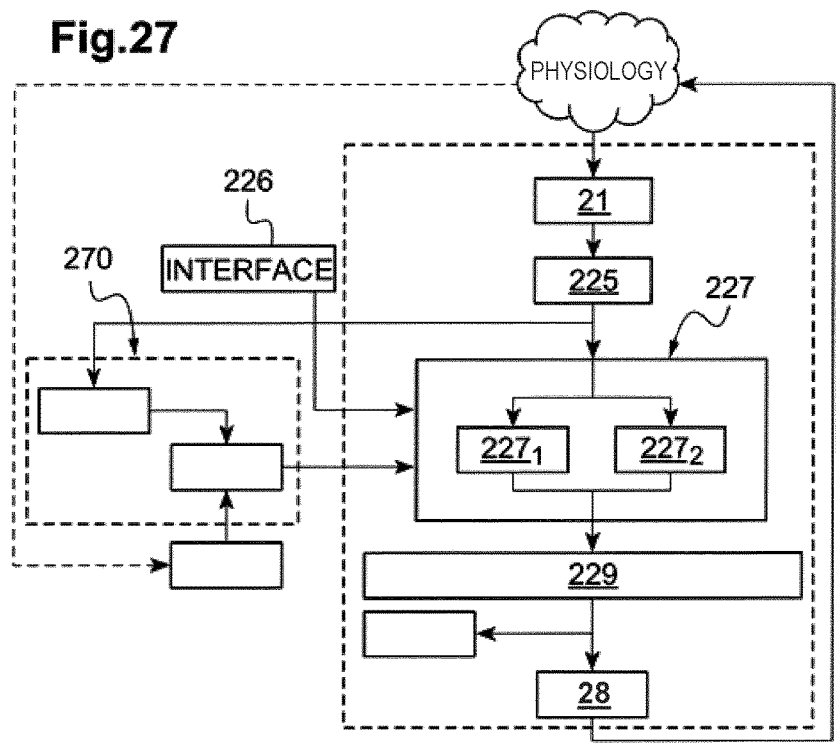
FIG. 27 shows the implementation of the architecture of FIG. 25 as part of a remote parameter estimation.

In a first embodiment, an estimate of the parameters is made in a remote external system 270 including the parameters reconfiguration module 252 and the analysis module 253, as illustrated in FIG. 27. This estimate is based on a scan of parameters and on an analysis of its effects, as described above. This estimate can be made intraoperatively or postoperatively during a follow-up session, using a remote analysis module.

Figure 28:
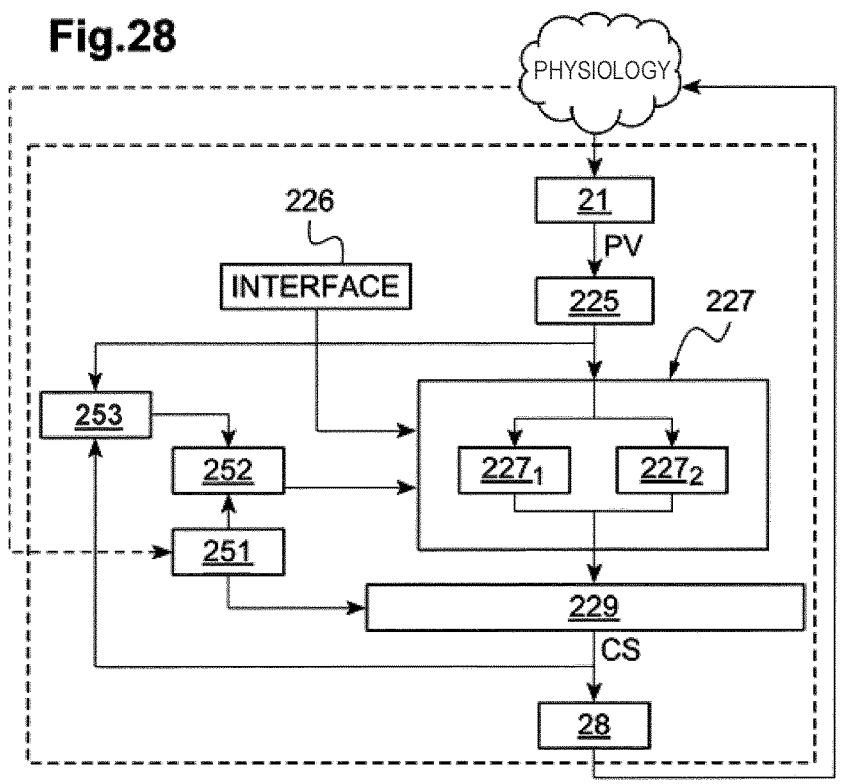
FIG. 28 shows the implementation of the architecture of FIG. 25 as part of a parameter integrated estimation.

In a second embodiment, illustrated in FIG. 28, an adaptive estimation of the parameters is carried out in an integrated manner, that is to say that the update of the values RS and the reorganization of the transition matrix T are formed within the implantable device, which implies that the analysis module 253 and the reconfiguration module 252 are embedded in the implantable device.

Thus the implantable device is auto-adaptive and autonomously applies a learning of typical values.

In summary, the adaptive estimation feature of parameters is a refinement of the state transition control system described in the foregoing, whether it is implemented on a deterministic, stochastic base, or on a set of control devices combining the deterministic and stochastic approaches.

In the case of adaptation according to several remote temporal resolutions, with the embodiment of FIG. 27, the adaptation of the state transition model can be performed at different temporal resolutions such as, but not limited to, n times per day, n times per week, n times a month, n times per year, programmed by the practitioner with a corresponding track.

In the case of the integrated embodiment form corresponding to FIG. 28, the adaptation of the state transition model can be implemented with different temporal resolutions such as, but not limited to, n times per hour, n times per day, daily, once a week, once a month, once a year.

In this sense, the embodiment of FIG. 28 can be used to adapt control devices dedicated to the regulation of physiological variables in the short term (e.g., RR interval, peaks of blood pressure variation (dP/dt)$_{max}$, physical activity) and to the regulation of physiological variables that change in the long-term (e.g. heart rate HR, variability of heart rate HRV).

In addition, the embodiment of FIG. 27 can be used to adapt the state transition control devices dedicated to the regulation of physiological variables in the long term.

What is claimed is:

1. A pacing therapy system, comprising:
an external communication device;
a stimulation device adapted to communicate with the external device, the stimulation device comprising:
one or more electrodes adapted to be placed on or near a nerve of an autonomic nervous system;
a sensor that senses at least one of a physiological signal or a physical signal;
a processing circuit that provides at least one of a current physiological level or a current physical level using the sensor; and
a control circuit that causes the stimulation device to provide a stimulation according to a set of stimulation parameters, the control circuit comprising a memory having a state transition model comprising a transition matrix and a connection matrix stored thereon, the transition matrix defining conditions for transitioning between particular states of a plurality of states of the state transition model and the connection matrix defining whether transitions between particular pairs of states are permitted, wherein the plurality of states are defined by a set of stimulation parameters and at least one of an expected physiological response or an expected physical response during application of the stimulation with the set of stimulation parameter values, and wherein the control circuit is adapted to use the state transition model to modify stimulation parameters to bring the at least one of the current physiological level or the current physical level to a reference level, wherein the control circuit is adapted to use the state transition model to modify the stimulation parameters using a self-adapting procedure by:
successively storing at least one of an actual physiological level or an actual physical level achieved during delivering of the stimulation according to the set of stimulation parameters;
adjusting the at least one of the expected physiological response or the expected physical response associated with the set of stimulation parameters according to the at least one of the actual physical level or the actual physiological level achieved during the stimulation with said set of stimulation parameters to obtain new values for the plurality of states; and
ordering the plurality of states based on the new values of the at least one of the expected physiological response or the expected physical response to determine the states to which to transition.

2. The system of claim 1, wherein the new value of the at least one of the expected physiological response or the expected physical response of a state of the state transition model is calculated from an average of the at least one of the actual physiological level or the actual physical level recorded during the stimulation with the set of stimulation parameters.

3. The system of claim 1, wherein the self-adapting procedure further comprises calculating the new value of the at least one of the expected physiological response or the expected physical response of a state of the state transition model from an average of the at least one of the current physiological level or the current physical level and a current value of the at least one of the expected physiological response or the expected physical response.

4. The system of claim 1, wherein the self-adapting procedure further comprises calculating the new value of the at least one of the expected physiological response or the expected physical response of the state of the state transition model using an artificial intelligence model between successive current physiological levels or current physical levels and a current value of the at least one of the expected physiological response or the expected physical response.

5. The system of claim 1, wherein the self-adapting procedure is triggered by the external communication device.

6. The system of claim 5, wherein the control circuit is adapted to:
trigger stimulation sequences in the stimulation device in response to input from an operator using the external communication device; and
transmit the at least one of successive physiological levels or the physical levels, in response to the sets of stimulation parameters, to the external communication device; and
wherein the external communication device:
determines the new values of the at least one of the expected physiological response or the expected physical response;
sorts the states based on the new values of the at least one of the expected physiological response or the expected physical response; and
transfers the new states with associated data pairs to the stimulation device, each data pair comprising a set of stimulation parameters and at least one of an expected physiological response or an expected physical response.

7. The system of claim 1, wherein the self-adapting procedure is triggered by the stimulation device at predetermined regular intervals.

8. The system of claim 1, wherein the self-adapting procedure is triggered by the stimulation device during an occurrence of a predefined event.

9. The system of claim 1, wherein the sensor detects at least one of a cardiac, muscular or nervous electrogram signal; a body, cardiac or muscular acceleration signal; a respiratory bioimpedance signal; a blood flow or blood pressure signal; a temperature signal; a piezometric pressure signal; or a cardiac contractility signal.

10. The system of claim 9, wherein the at least one of the current physiological level or the current physical level is determined from a variable corresponding to at least one of: a heart rate variability of sinus rhythm, a blood pressure, a cardiac contractility, a physical activity, a temperature, a movement or a respiratory rate.

11. A method of applying a pacing therapy to a nerve of the autonomic nervous system with a stimulation device, the method comprising:
generating a state transition model comprising a plurality of states defined by a set of stimulation parameters and at least one of an expected physiological response or an expected physical response during application of a stimulation with the set of stimulation parameters;

sensing at least one of a current physiological signal or a current physical signal;

determining at least one of a current physiological level or a current physical level based on the at least one of the current physiological signal or the current physical signal; and determining a set of stimulation parameters to bring the at least one of the current physiological level or the current physical level to a reference level by:

successively delivering stimulation to the nerve according to sets of stimulation parameters associated with the plurality of states;

storing at least one of an actual physiological level or an actual physical level achieved during delivery of the stimulation according to the successive sets of stimulation parameters;

adjusting the at least one of the expected physiological response or the expected physical response associated with the set of stimulation parameters in the state transition model for the plurality of states according to the at least one of the actual physiological level or the actual physical level achieved during delivery of sets of stimulation parameters to obtain at least one of a new expected physiological response or a new expected physical response; and ordering the plurality of states based on the at least one of the new physiological response or the new physical response to determine the states to which to transition.

12. The method of claim 11, wherein adjusting the at least one of the expected physiological response or the expected physical response comprises calculating the at least one of the new expected physiological response or the new expected physical response of a given state of the state transition model from an average of at least one of the actual physiological level or the actual physical level recorded during the stimulation with the set of stimulation parameters.

13. The method of claim 11, wherein adjusting the at least one of the expected physiological response or the expected physical response comprises calculating the at least one of the new expected physiological response or the new expected physical response of a given state of the state transition model from an average of the at least one of the current physiological level or the current physical level and a current value of the at least one of the expected physiological response or the expected physical response.

14. The method of claim 11, wherein adjusting the at least one of the expected physiological response or the expected physical response comprises calculating the at least one of the new expected physiological response or the new expected physical response of a given state of the state transition model using an artificial intelligence model between successive current physiological levels or current physical levels and a current value of the at least one of the expected physiological response or the expected physical response.

15. The method of claim 11, wherein determining the set of stimulation parameters to bring the at least one of the current physiological level or the current physical level to the reference level is triggered by an external communication device capable of communicating with the stimulation device.

16. The method of claim 15, further comprising:

triggering stimulation sequences in the stimulation device is response to input from an operator using the external communication device;

transmitting the at least one of the actual physiological level or the actual physical level in response to the sets of stimulation parameters, to the external communication device;

determining, by the external communication device, the at least one of the new expected physiological response or the new expected physical response;

sorting, by the external communication device, the plurality of states based on the at least one of the new expected physiological response or the new expected physical response; and transferring, from the external communication device, a plurality of new states with associated data pairs to the stimulation device, each data pair comprising a set of stimulation parameters and at least one of an expected physiological response or an expected physical response.

17. The method of claim 11, wherein determining the set of stimulation parameters to bring the at least one of the current physiological level or the current physical level to the reference level is triggered by the stimulation device at predetermined regular intervals.

18. The method of claim 11, wherein determining the set of stimulation parameters to bring the at least one of the current physiological level or the current physical level to the reference level is triggered by the stimulation device during an occurrence of a predefined event.

19. The method of claim 11, wherein the at least one of the current physiological signal or the current physical signal is at least one of a cardiac, muscular or nervous electrogram signal; a body, cardiac or muscular acceleration signal; a respiratory bioimpedance signal; a blood flow or blood pressure signal; a temperature signal; a piezometric pressure signal; or a cardiac contractility signal.

20. The method of claim 19, wherein at least one of the current physiological level or the current physical level is determined from a variable corresponding to at least one of a heart rate variability of sinus rhythm, a blood pressure, a cardiac contractility, a physical activity, a temperature, a movement or a respiratory rate.

21. A pacing therapy device comprising:

a stimulation device; and a control circuit that causes the stimulation device to provide a stimulation to a nerve of an autonomic nervous system according to a set of stimulation parameters, the control circuit comprising a memory having a state transition model comprising a transition matrix and a connection matrix stored thereon, the transition matrix defining conditions for transitioning between particular states of a plurality of states of the state transition model and the connection matrix defining whether transitions between particular pairs of states are permitted, wherein the plurality of states are defined by a set of stimulation parameters and at least one of an expected physiological response or an expected physical response during application of the stimulation with the set of stimulation parameter values, and wherein the control circuit is adapted to use the state transition model to modify stimulation parameters to bring the at least one of a current physiological level or a current physical level to a reference level, wherein the control circuit is adapted to use the state transition model to modify the stimulation parameters using a self-adapting procedure by:

successively storing at least one of an actual physiological level or an actual physical level achieved during delivering of the stimulation according to the set of stimulation parameters;

adjusting the at least one of the expected physiological response or the expected physical response associated with the set of stimulation parameters according to the at least one of the actual physical level or the actual physiological level achieved during the stimulation with said set of stimulation parameters to obtain new values for the plurality of states; and ordering the plurality of states based on the new values of the at least one of the expected physiological response or the expected physical response to determine the states to which to transition.

* * * * *